US012694983B2

(12) United States Patent　　　　　　(10) Patent No.:　US 12,694,983 B2
Lambert et al.　　　　　　　　　　　　　(45) Date of Patent:　　Jul. 28, 2026

(54) SYSTEMS, METHODS, AND DEVICES FOR MELANOMA PATHOLOGY USING ONE OR MORE NEURAL NETWORKS

(71) Applicant: Pathology Watch Inc., Murray, UT (US)

(72) Inventors: Daniel Lambert, Salt Lake City, UT (US); James Requa, Sherman Oaks, CA (US); Jeffery Hester, Overland Park, KS (US)

(73) Assignee: Pathology Watch Inc., Murray, UT (US)

( * ) Notice: Subject to any disclaimer, the term of this patent is extended or adjusted under 35 U.S.C. 154(b) by 539 days.

(21) Appl. No.: 18/189,965

(22) Filed: Mar. 24, 2023

(65) Prior Publication Data

US 2024/0321449 A1　　Sep. 26, 2024

(51) Int. Cl.
　　　*G16H 50/20*　　　　　(2018.01)
(52) U.S. Cl.
　　　CPC .................................. *G16H 50/20* (2018.01)
(58) Field of Classification Search
　　　None
　　　See application file for complete search history.

(56) References Cited

U.S. PATENT DOCUMENTS

2006/0149162 A1　7/2006　Daw et al.
2007/0122797 A1　5/2007　De La Torre-Bueno
2009/0131819 A1　5/2009　Ritchie et al.

2010/0022912 A1　1/2010　Fehre et al.
2010/0238043 A1　9/2010　Wakamiya et al.
2012/0290310 A1　11/2012　Watson
2014/0379615 A1　12/2014　Brigham et al.
2015/0324522 A1　11/2015　Chan et al.
2016/0085913 A1　3/2016　Evans et al.
2016/0364630 A1　12/2016　Reicher et al.
2017/0220775 A1　8/2017　De La Torre-Bueno
　　　　　　　　　(Continued)

FOREIGN PATENT DOCUMENTS

WO　　　2007078842 A1　　7/2007

OTHER PUBLICATIONS

Goes et al., "A Process for Human Resource Performance Evaluation Usin Computational Intelligence: An Approach Using a Combination of Rule-Based Classifiers and Surpervised Learning Algorithms," IEEE Access, Jan. 29, 2020, 17 pages.

(Continued)

*Primary Examiner* — Daniel T Tekle
(74) *Attorney, Agent, or Firm* — Haynes and Boone LLP

(57)　　　　　　ABSTRACT

Systems, methods, and devices, for melanoma pathology using one or more neural networks (NNs). The techniques described herein may include receiving molecular data corresponding to a patient biopsy sample; molecular data; encoding molecular output data according to a preselected encoding scheme; receiving image data corresponding to the patient biopsy sample; applying the image data to an image analysis NN; concatenate the encoded molecular data to the image data at an intermediate layer of the image analysis NN; and producing, based on the encoded molecular information and the image information concatenated at the intermediate layer, a prognosis output from the image analysis NN. Many other features and examples are described herein.

39 Claims, 12 Drawing Sheets

(56)  References Cited

U.S. PATENT DOCUMENTS

| | | | | |
|---|---|---|---|---|
| 2020/0075169 | A1* | 3/2020 | Lau | G16H 30/00 |
| 2020/0105413 | A1* | 4/2020 | Vladimirova | G16H 20/30 |
| 2020/0380675 | A1 | 12/2020 | Golden et al. | |
| 2020/0381103 | A1 | 12/2020 | Froloff | |
| 2020/0400930 | A1 | 12/2020 | D'Costa et al. | |
| 2021/0350930 | A1* | 11/2021 | Baron | G06N 20/20 |
| 2021/0407634 | A1 | 12/2021 | Lyman et al. | |
| 2022/0084660 | A1 | 3/2022 | Georgescu et al. | |
| 2022/0285032 | A1* | 9/2022 | Covington | G16H 50/30 |
| 2022/0405932 | A1* | 12/2022 | Gaskill-Shipley | A61B 5/055 |
| 2023/0044399 | A1 | 2/2023 | Shochat et al. | |
| 2023/0061099 | A1 | 3/2023 | Cummings | |
| 2023/0352187 | A1 | 11/2023 | Schaper et al. | |
| 2024/0118297 | A1 | 4/2024 | Rapuano et al. | |

OTHER PUBLICATIONS

International Search Report and Written Opinion for Application No. PCT/US2024/042292, mailed Nov. 6, 2024, 20 pages.
International Search Report and Written Opinion for Application No. PCT/US2024/042273, mailed Oct. 10, 2024, 19 pages.
Schmidt et al., "Integration of Scanned Document Management With the Anatomic Pathology Laboratory Information System: Analysis of Benefits," American Journal of Clinical Pathology, 2006, 6 pages.
International Search Report and Written Opinion for Application No. PCT/US2024/20732, mailed Jul. 2, 2024, 13 pages.
Sepulveda et al., "The Ideal Laboratory Information System," Archives of Pathology and Laboratory Medicine, 2013, 12 pages.

\* cited by examiner

700

| EXAMPLE BIOMARKERS |
| :---: |
| <TOR1AIP1, BAP1, MGP, SPP1, CXCL14, CLCA2, S100A8, BTG1, SAP130, ARG1, KRT6B, GJA1, ID2, EIF1B, S100A9, CRABP2, KRT14, ROBO1, RBM23, TACSTD2, DSC1, SPRR1B, TRIM29, AQP3, TYRP1, PPL, LTA4H, and CST6> |

800

| EXAMPLE PATIENT INFORMATION AND/OR CLINICAL NOTES DATA |
|---|
| Date of Birth:<br>Age at Diagnosis:<br>Sex (Female, Male or Unknown):<br>Race, if available:<br>Fitzpatrick Skin Color, if available:<br>Breslow Thickness:<br>Ulceration (Absent, Present or Unknown):<br>Mitotic Rate $\leq 1/mm^2$ or $> /mm^2$:<br>Node Status (Positive or Negative):<br>AJCC Stage (None, I, IA, IB, IIA, IIB, IIC, III, IIIA, IIIB, or IV):<br>T Stage:<br>Date of Biopsy of Primary Melanoma:<br>Location of Primary Tumor (Head and Neck, Trunk, Extremity, or Unknown):<br>Date of Follow-up Visits:<br>Follow-up (Event-free or Event):<br>Location of First Recurrence (Nodal/regional or Distant):<br>Time to Recurrence (Years):<br>SLNB Status (Positive, Negative or Unknown):<br>Personal medical history:<br>Family medical history:<br>Medication list:<br>Allergies:<br>Has the patient had multiple primary melanomas?<br>Radiology results after the primary melanoma biopsy |

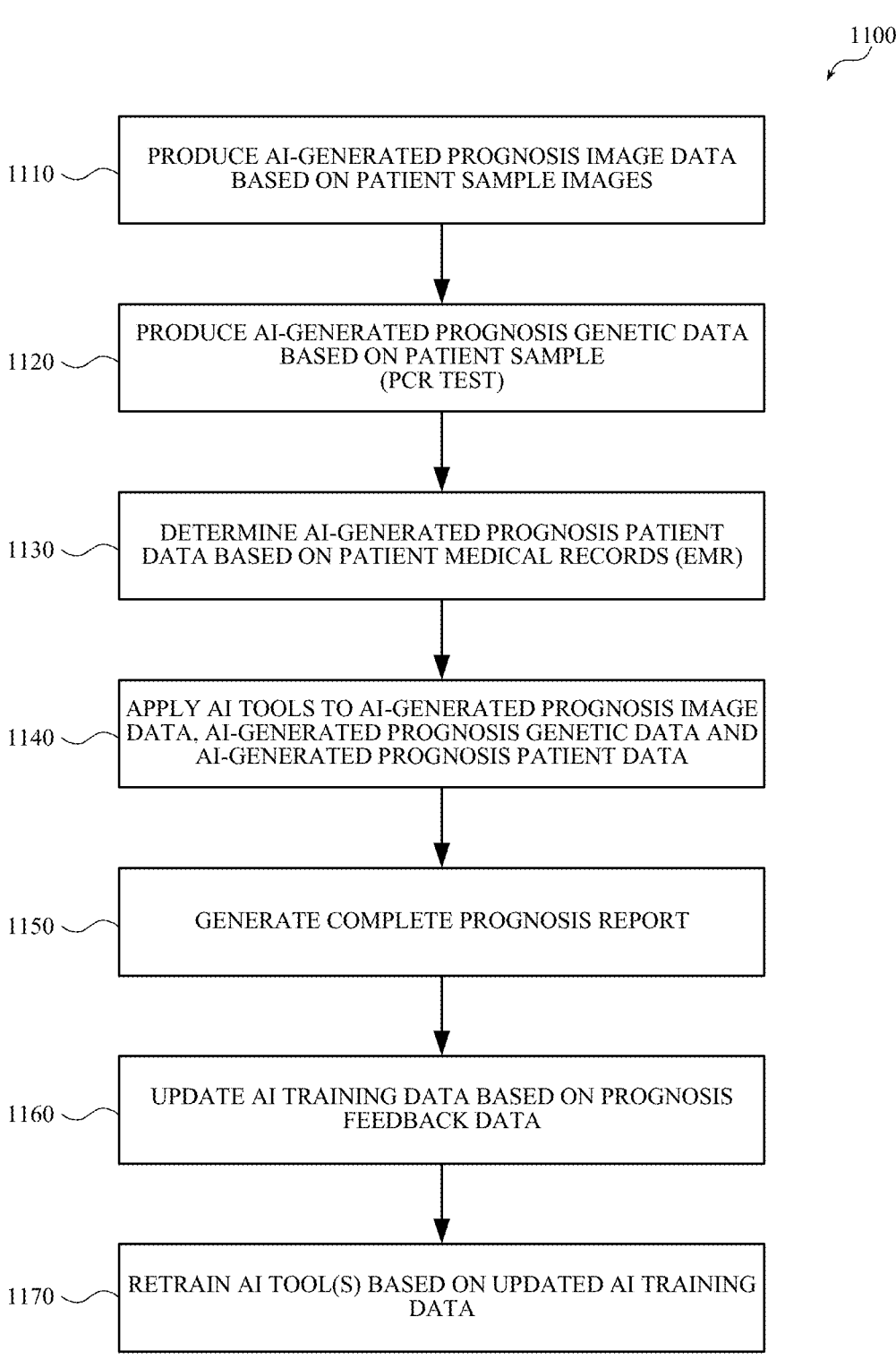

1100

1110 — PRODUCE AI-GENERATED PROGNOSIS IMAGE DATA BASED ON PATIENT SAMPLE IMAGES

1120 — PRODUCE AI-GENERATED PROGNOSIS GENETIC DATA BASED ON PATIENT SAMPLE (PCR TEST)

1130 — DETERMINE AI-GENERATED PROGNOSIS PATIENT DATA BASED ON PATIENT MEDICAL RECORDS (EMR)

1140 — APPLY AI TOOLS TO AI-GENERATED PROGNOSIS IMAGE DATA, AI-GENERATED PROGNOSIS GENETIC DATA AND AI-GENERATED PROGNOSIS PATIENT DATA

1150 — GENERATE COMPLETE PROGNOSIS REPORT

1160 — UPDATE AI TRAINING DATA BASED ON PROGNOSIS FEEDBACK DATA

1170 — RETRAIN AI TOOL(S) BASED ON UPDATED AI TRAINING DATA

*FIG. 11*

SYSTEMS, METHODS, AND DEVICES FOR MELANOMA PATHOLOGY USING ONE OR MORE NEURAL NETWORKS

FIELD

This disclosure relates to electronic systems and devices, neural networks, and melanoma pathology.

BACKGROUND

When a patient is diagnosed with cancer, such as melanoma, prognostic evaluation and testing is commonly performed. Prognostic testing can involve a biopsy sample being analyzed visually and genetically. When accurate, prognostic testing may enable the physician and patient to better understand the severity of the cancer, a treatment methodology, the likelihood of recurrence, and other possibilities. An accurate prognosis may better enable the physician and patient to work together and develop a suitable treatment plan.

BRIEF DESCRIPTION OF THE DRAWINGS

The present disclosure will be readily understood and enabled by the detailed description and accompanying figures of the drawings. Like reference numerals may designate like features and structural elements. Figures and corresponding descriptions are provided as non-limiting examples of aspects, implementations, etc., of the present disclosure, and references to "an" or "one" aspect, implementation, etc., may not necessarily refer to the same aspect, implementation, etc., and may mean at least one, one or more, etc.

FIG. 8 is a diagram of an example of patient data and clinical notes data according to one or more implementations described herein.

FIG. 11 is a diagram of an example process for melanoma pathology according to one or more implementations described herein.

DETAILED DESCRIPTION

Figure 1:
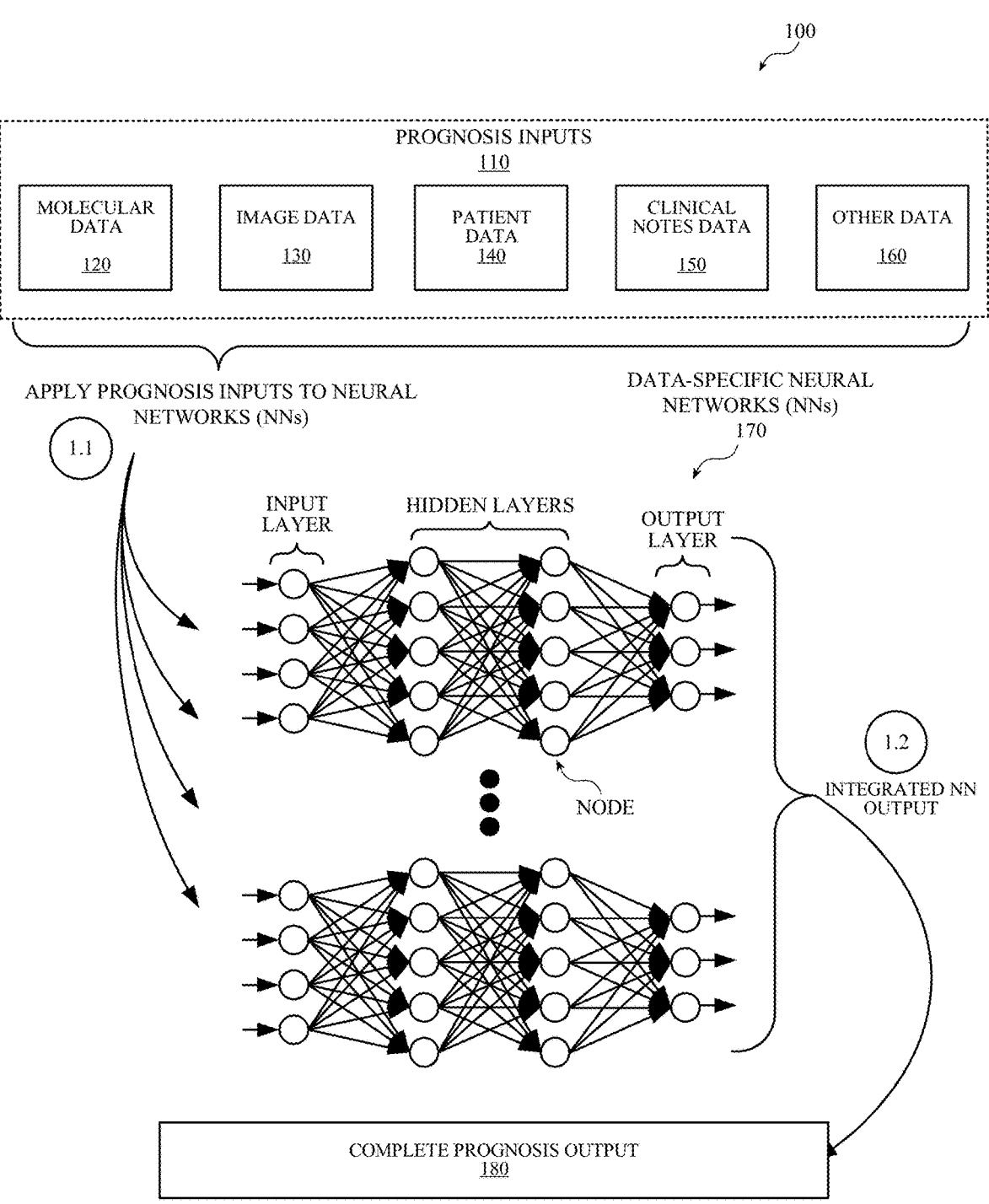
FIG. 1 is a diagram of an example overview of one or more implementations described herein.

The following detailed description refers to the accompanying drawings. Like reference numbers in different drawings may identify the same or similar features, elements, operations, etc. Additionally, the present disclosure is not limited to the following description as other implementations may be utilized, and structural or logical changes made, without departing from the scope of the present disclosure.

Each year, hundreds of thousands of people develop melanoma. Melanoma may begin as a treatable condition, but when left undetected or poorly treated, it may metastasize, require painful and prolonged treatment, and result in death. Timely and effective healthcare may therefore be the difference between life or death. Nevertheless, many people lack the physical or financial means to access healthcare. The costs of healthcare can be so high in some countries that it is not uncommon for patients with serious conditions to be forced to choose between paying for healthcare, housing, or another fundamental aspect of life. Even for those living in areas with highly capable physicians and sophisticated hospitals, the costs alone may be a prohibitive factor for accessing healthcare.

Further, those with access to healthcare are not guaranteed to receive a quality of care commensurate with the threat and implications of a serious disease like melanoma—implications for the patient and friends and family as well. Indeed, being able to see a doctor and pay for treatment is no guarantee that a diagnosis will be correct or that treatment will be effective. The misdiagnosis or improper treatment of a serious disease may result in anything ranging from an otherwise completely preventable death, prolonged and unnecessary emotional pain, mental stress, and significant medical bills. For these and other reasons, society has a significant and ongoing interest in technological advancements that improve the accessibility and the quality of healthcare.

Notwithstanding, such developments are elusive. An increase in accessibility often comes at the expense of quality, and an increase in quality often comes at the expense of accessibility. Reducing costs by relaxing medical practice standards may lead to an increase in misdiagnoses and improper treatment. By contrast, a groundbreaking medical procedure may lead to a more effective treatment, but such treatments are often so expensive as to be largely inaccessible to the general public. These deficiencies—a reduction in quality or inaccessibility—can be especially disconcerting for time-sensitive and potentially life-threatening conditions, such as melanoma. Indeed, society's considerable interest in healthcare advancements that increase both accessibility and quality, combined with the scarcity of such advancements, highlights the challenges and barriers in conceiving, developing, and reducing them to practice.

Additionally, the diagnosis, prognosis, and treatment of melanoma may involve using different types of information accessible via different technologies. For instance, imaging technology may be used to capture visual data of a sample from different angles, levels of detail, and so on. Digital patient records and information systems may be used to ascertain qualitative factors about the patient's condition, such as whether there is a history of a disease in a family, whether the patient has physical characteristics that may be relevant to a disease, or whether dietary or lifestyle decisions of a patient may be relevant to a disease. As another example, a patient may undergo genetic testing designed to indicate whether a patient's genetics may be relevant to a disease.

While these distinct technologies may each generate information relevant to a disease like melanoma, the types of information produced do not naturally interrelate in a self-evident manner fit for collective analysis. As a result, doctors and institutions may, whether by habit, outdated information, unwitting policy, poor practices, etc., improperly assign levels of significance to different types of data or subsets of data. For example, some practitioners may assign too much significance to genetic data and too little significance to imaging and patient data. Other practitioners may err by being unjustifiably partial to certain subsets of data. For instance, some physicians may consider a specific subset of genetic data in the presence of a particular subset of patient data (e.g., a skin type) to be dispositive—regardless of contradictory genetic data, patient data, and image data.

Consequently, different physicians and institutions can experience different rates of success and failure because data is being evaluated and used in different ways. And failure to assign a proper significance to different combinations of data increases the chances that healthcare services are provided and paid for unnecessarily; or worse, that necessary healthcare services are neither offered nor provided to begin with. Accordingly, while certain physicians or institutions may consider different types of information in melanoma cases, current technology fails to provide a solution that addresses some or all of the deficiencies descried above. That is, current technology fails to provide a fully integrating analysis of disparate types of data in a manner that enables an efficient, accurate, consistent, and comprehensive approach, to melanoma pathology.

The techniques described herein include significant technological advancements that increase the accessibility and quality of healthcare, including the diagnosis, prognosis, and treatment of melanoma. These techniques may increase accessibility to healthcare by rendering, as unnecessary or obsolete, costly and cumbersome diagnostic and testing procedures that are typically used. The techniques described herein may also enhance the quality of healthcare by increasing the accuracy of diagnosing and prognosticating melanoma, and by consequence the effectiveness of treatment as well. One or more of the techniques described herein may include the prediction of the growth and/or spreading patterns of melanoma.

As described, these benefits may be achieved by normalizing distinct types of data (e.g., image data, patient data, genetic data, etc.) into individual sets of neural network training data. The training data may be used to train individual neural networks and assign a weight or significance to individual elements, and combinations of elements, for each set of training data. The weighted elements and element combinations from each data set may be applied to a centralized neural network. The individual sets of neural network training data may be combined into a centralized set of neural network training data and used to train the centralized neural network. Different types of neural networks (e.g., a graph neural network, a convolutional neural network, etc.) may be used for different types of training data.

In some implementations, neural network tools may be applied to training data to rapidly increase the volume of valid training data. For example, multiple variations of an image may be generated by applying neural network tools capable of creating a new image by modifying an existing image based on instructions received via text. In some implementations, neural network tools may be applied to enhance the robustness of neural network layers. For example, a neural network may be trained on image data, and patient data and/or genetic data may be introduced to a layer of the neural network (e.g., a penultimate layer) to increase the robustness of the layer and neural network output accuracy. Details and examples of these and other techniques are described below with reference to the Figures.

FIG. 1 is a diagram of an example overview of one or more implementations described herein. As shown, prognosis inputs 110 may include molecular data 120, image data 130, patient data 140, clinical notes data 150, and other data 160.

Molecular data 120 may include genetic information, biological markers, and other types of biological information extracted from a physical biopsy sample. Image data 130 may include digitized graphical information of the physical biopsy sample at varying microscopic levels and detail as well as graphical information about the tumor microenvironment, such as the size of lymphocytes, inflammation, or structures. This information may be obtained manually by using a microscope or algorithmically using a digital whole slide image (WSI) scanner. Patient data 140 may include medical information of a patient of the physical biopsy sample, such as age, gender, medical history, Breslow depth, Fitzpatrick skin type, AJCC score, family history scoring, etc. Clinical notes data 150 may include clinical information submitted by one or more physicians, or other medical experts, regarding the patient and/or the physical biopsy sample. Other data 160 may include one or more other types of information relevant to providing an accurate pathology for the patient and biopsy sample.

Prognosis inputs 110 may be applied to one or more neural networks (NNs) 170 for analysis and synthesis (at 1.1). NNs 170 may each include an input layer, one or more hidden layers, and an output layer. Each type of prognosis inputs 110 may be applied to a data-specific NN that is trained or modeled according to the corresponding type of information. For example, molecular data 120 may be applied at an input layer to a NN trained to evaluate genetic sequences, biomarkers, etc.; image data 130 may be applied at an input layer to a NN trained to evaluate image information; and so on. An output of each of NNs 170 may be an evaluation of the patient and biopsy sample regarding melanoma.

Layers of NNs 170 may be integrated such that the combined output of NNs 170 is a complete prognosis output 180 resulting from all of prognosis inputs 110 and data-specific NNs 170 (at 1.2). For instance, an output of a NN applied to molecular data 120, an output of a NN applied to patient data 140, and an output of a NN applied to clinical notes data 150 may be concatenated or applied to a hidden or intermediate layer of a NN applied to image data 130. Doing so may modify a weight or predictive significance of one or more intermediate nodes of the NN applied to image data 130, and in turn produce a more complete prognosis derived from multiple types of data and augmented by machine learning and artificial intelligence. Additional details and examples are discussed below with reference to the Figures.

Figure 2:
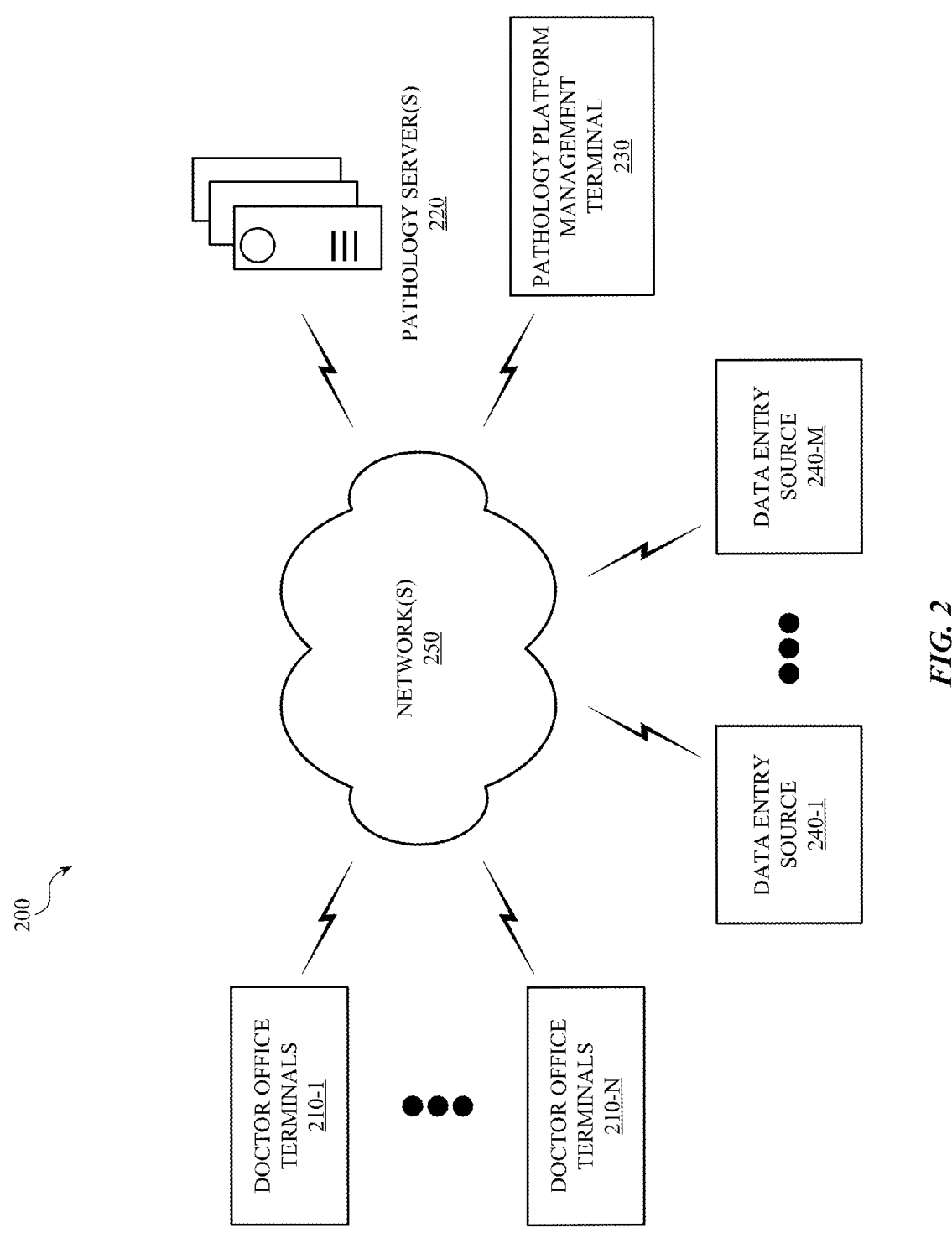
FIG. 2 is a diagram of an example network according to one or more implementations described herein.

FIG. 2 is a diagram of an example environment 200 in which systems and/or methods, described herein, may be implemented. As depicted, environment 200 may include doctor office terminals 210-1, . . . 210-N (where N is greater than or equal to 2 and collectively referred to as "terminals 210"), pathology servers 220, platform management terminal 230, data entry sources 240-1, . . . 240-M (where M is greater than or equal to 2 and collectively referred to as "sources 240"), and network 250. The number of devices and/or network, illustrated in FIG. 2, is provided for explanatory purposes only. In practice, there may be additional devices and/or networks, fewer devices and/or networks, different devices and/or networks, or differently arranged devices and/or networks than illustrated in FIG. 2. Devices of environment 200 may interconnect via wired connections, wireless connections, or a combination of wired and wireless connections. Also, one or more of the devices of environment 200 may perform one or more functions described as being performed by one or more other devices of environment 200.

Terminal 210 may include any type of computing and communication device capable of communicating with network 250. For example, terminal 210 may include a smartphone, tablet computer, laptop computer, wearable device, etc. Terminal 210 may alternatively include a desktop computer, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), or another type of computation or communication device. Terminal 210 may include any variety of peripheral devices, such as speakers, cameras, external storage devices, etc. Terminal 210 may include an operating system and a browser, or another type of application or interface, capable of accessing network 250. Terminal 210 may enable a physician, administrator, or another type of user to access and interface with services supported by pathology servers 220, such as account creation, account management, information upload and download, etc.

Pathology servers 220 may include one or more servers or other types of computing devices capable of gathering, processing, searching for, storing, and/or communicating information as described herein. Pathology servers 220 may communicate with doctor office terminals 210, pathology platform management terminal 230, data entry sources 230, and/or other devices, via network 250, to receive molecular data, image data, patient data, and/or clinical data and provide pathology results based on the data received. Pathology servers 220 may be configured to train and apply multiple NNs. As described herein, some NNs may be data-specific (e.g., designed for a certain type of data), while others may be an integrated NN that draws upon the functionality and output of other NNs. In some implementations, pathology servers 220 may support a platform of services relating to pathology services, including user and account creation, security policies, data storage, billing services, usage metrics, and more.

Pathology platform management terminal 230 may include any type of wired or wireless user device capable of communicating with pathology servers 220 via network 250. Pathology platform management terminal 230 may include a smartphone, tablet computer, laptop computer, desktop computer, or another type of user device capable of enabling a user, operator, administrator, or developer to interact with pathology servers 220. Additionally, or alternatively, pathology platform management terminal 230 may be directly connected to pathology servers 220. Pathology platform management terminal 230 may be a laboratory information system (LIS) configured to track samples, barcodes of samples, and/or one or more other types of sample identifiers through the laboratory processing. Pathology platform management terminal 230 may be configured to support, perform, or enable the management of a pathology image.

Data entry source 240 may include one or more types of computer and communication devices, including a user device, server device, data storage device, or another type of device capable of providing one or more types of data to pathology servers 220. Data entry source 240 may include one or more servers that receives, stores, and provides medical records, such as patient data and clinical notes. Additionally, or alternatively, data entry source 240 may include a polymerase chain reaction (PCR) system or machine capable of performing a PCR test and communicating the results of the test to pathology servers 220. Data entry source 240 may implement one or more security or information security protocols to ensure that medical records are properly procured, stored, and maintained. In some implementations, data entry source 240 may implement data anonymization to ensure that medical records are properly anonymized.

Network 250 may include a single network or multiple networks capable of enabling a connection between the devices of FIG. 2. Network 250 may include one or more wired and/or wireless networks. For example, network 250 may include a Bluetooth® network, a Wi-Fi network, or a cellular network, the Public Land Mobile Network (PLMN), and/or a second generation (2G) network, a third generation (3G) network, a fourth generation (4G) network, a fifth generation (5G) network, a sixth generation (6G) network and/or another type of network. Additionally, or alternatively, network 250 may include a wide area network (WAN), a metropolitan area network (MAN), an ad hoc network, an intranet, the Internet, a virtual network (e.g., a virtual private network (VPN)), a telephone network (e.g., a Public Switched Telephone Network (PSTN)), a Voice over IP (VOIP) network, and/or a combination of these or other types of networks.

Figure 3:
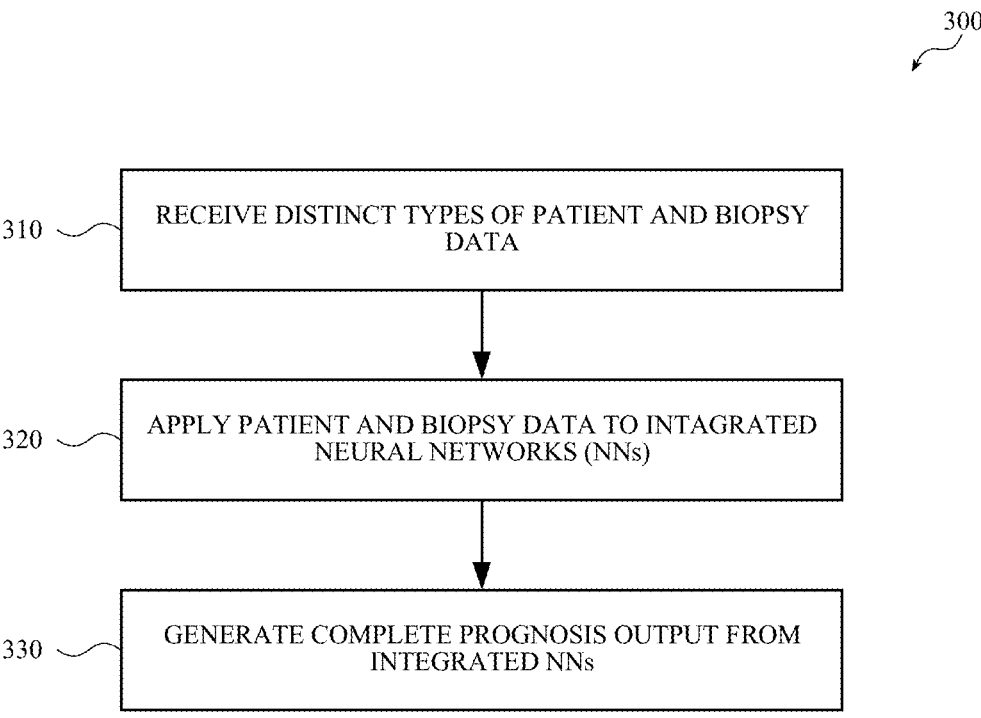
FIG. 3 is a diagram of an example process for melanoma pathology using different types of data as neural network (NN) inputs and an integrated NN according to one or more implementations described herein.

FIG. 3 is a diagram of an example process 300 for melanoma pathology analysis using different types of data as NN inputs and an integrated NN according to one or more implementations described herein. Process 300 may be implemented by pathology analysis servers 220. In some implementations, some or all of process 300 may be performed by one or more other systems or devices, including one or more of the devices of FIG. 1. Additionally, process 300 may include one or more fewer, additional, differently ordered and/or arranged operations than those shown in FIG. 3, including other processes and/or operations discussed herein. For example, process 300 may include operations preceding, performed in parallel with, and/or following one or more of the depicted operations. Furthermore, some or all of the operations of process 300 may be performed independently, successively, simultaneously, etc., of one or more of the other operations of process 300. As such, the techniques described herein are not limited to a number, sequence, arrangement, timing, etc., of the operations or process depicted in FIG. 3.

As shown, process 300 may include receiving distinct types of patient and biopsy data (block 310). For example, pathology servers 220 may receive molecular data, image data, patient data, clinical notes data, and more. Pathology analysis servers 220 may receive the data from one or more sources, such as doctor office terminals 210, data entry sources 240, and platform management terminal 230. One or more types of the data may also, or alternatively, be obtained from local or remote data storage repositories accessible by pathology analysis servers 220.

Molecular data may include genetic information, biological markers, and other types of biological information extracted from a biopsy sample. Image data may include digitized graphical information of the biopsy sample at varying microscopic levels and detail. Image data may include digitized graphical information of a biological environment and structures in and around the biopsy sample, such as a tumor, lymphocytes, blood vessels, tissue inflammation, etc. Patient data may include medical information of a patient of the physical biopsy sample, such as age, gender, Fitzpatrick's skin color, medical history, number, severity, and dates of prior instances of melanoma, etc. Clinical notes data may include clinical information submitted by one or more physicians, or other medical experts, regarding the patient and/or the physical biopsy sample.

Process 300 may include applying the patient and biopsy data to an integrated NN (block 320). For example, pathology servers 220 may apply patient and biopsy data to an integrated NN. An integrated NN may include a NN that combines or comprises learned features from NNs configured for different types of data, data analyses, and predictive capabilities. For example, an integrated NN may include or incorporate the learned features of a NN configured to evaluate molecular data from a biopsy, a NN configured to evaluate image data from the biopsy, a NN configured to evaluate patient data corresponding to the biopsy, and a NN configured to evaluate clinical notes data corresponding to the biopsy. As described herein, the learned features of one type of NN may be integrated into another type of NN by encoding and inclusion. For example, the output of a molecular analysis NN may be encoded and included into an intermediate layer of an image analysis NN, such that the nodes of the image analysis NN are modified or enhanced by the output of the molecular analysis NN. The output of a patient data NN and a clinical notes NN may be similarly encoded and included into the image analysis NN.

In some implementations, the integrated NN may be integrated via a voting technique applied to outputs of the different types of NNs. For example, if the molecular analysis NN outputs a value of 0.9 (e.g., 90%), the image analysis NN outputs a value of 0.7 (e.g., 70%), and the clinical notes NN outputs a value of 0.5 (e.g., 50%), pathology servers 220 may combine the outputs as a simple average (e.g., (0.9+0.7+0.5)/3=0.7). Alternatively, pathology servers 220 may combine the outputs using a weighted average, where each type of prediction is assigned, a weight representing the relative importance of each type of output in making an accurate prediction.

In one or more embodiments, the relevance of the different factors may be determined by a simple weighting and not by a neural network. Additionally, or alternatively, the relevance of the factors may be determined by certain factors being ranked high and others low (relative to an average, mean, or median value or range of values). For example, the molecular input may have some genes ranked high and some ranked low, and the NN may detect the presence of some features and the absence of other features. The combination of certain features being present with other features being absent (and/or undetected), across multiple data types, may enable a more accurate prediction.

Process 300 may include generating a complete prognosis output from the integrated NN (block 330). For example, pathology servers 220 may generate a complete prognosis output from the integrated NN. A complete prognosis output may include output information based on applying the distinct types of data (e.g., molecular data, image data, patient data, clinical notes data, etc.) to the integrated NN. The complete prognosis output may include one or more variables or values, including an indication of whether the biopsy sample includes melanoma, whether the melanoma is benign or malignant, a level of aggressiveness of the melanoma, and an estimated cancer stage. Additional examples of complete prognosis output may include a survival rate prediction, a probability or estimate of recurrence, an indication of whether and which additional biopsy samples should be studied, and more. In some implementations, the integrated NN may also output examples of other patient groups that had similar conditions as those of the current patient, and information describing the similarities and differences between the other patient groups and the current patient, including treatments and long-term outcomes of the other patient groups. In some implementations, complete prognosis output may include a recommendation on conducting a nearest node biopsy, a likelihood of metastasis, or a likelihood of recurrence of the melanoma. A nearest node biopsy may include the identification, removal, and examination of the lymphoid tissue to determine whether cancer cells have spread to the lymph node closest in proximity to the cancerous tumor.

Figure 4:
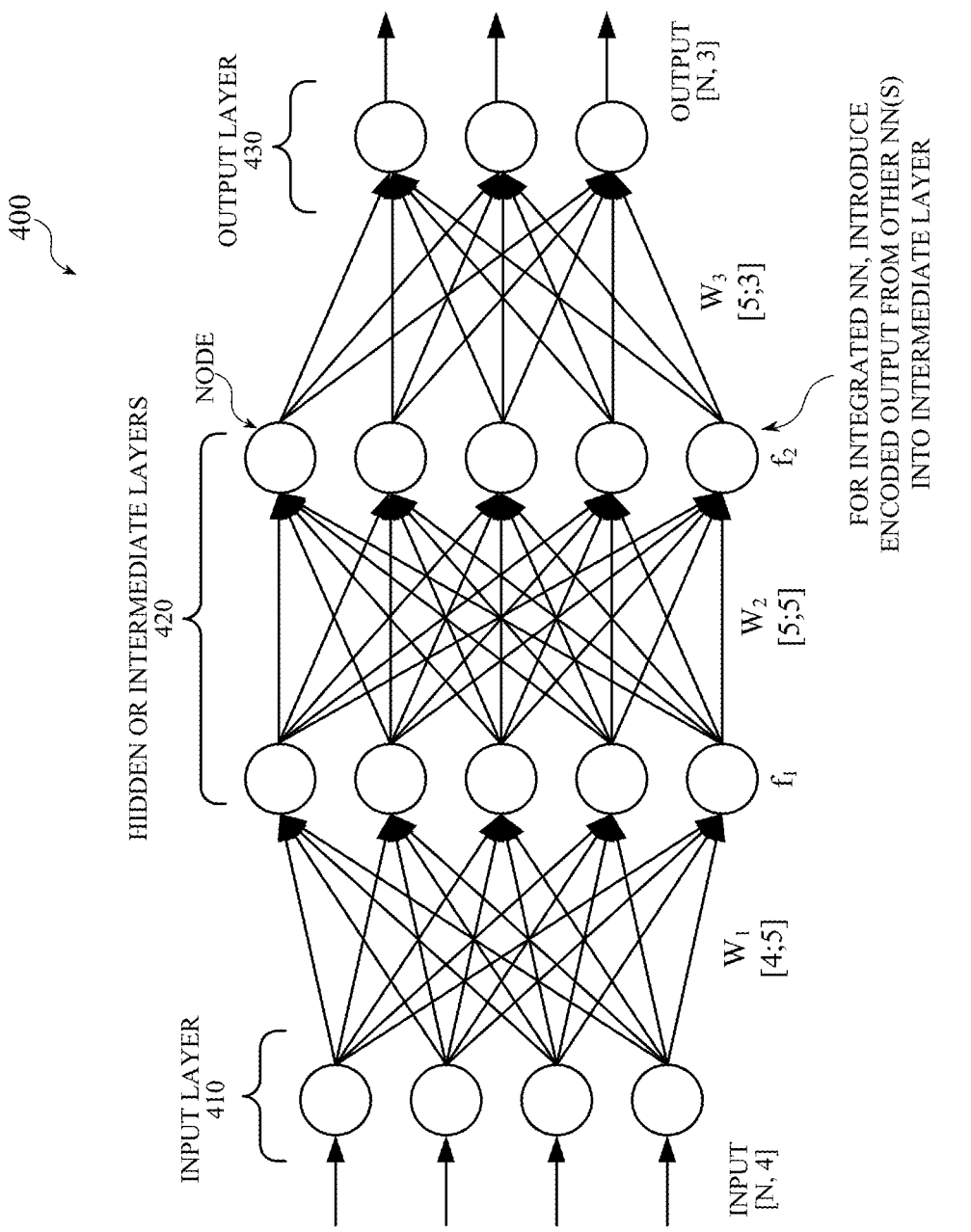
FIG. 4 is a diagram of an example of a NN according to one or more implementations described herein.

FIG. 4 is a diagram of an example of a NN 400 according to one or more implementations described herein. As shown, NN 400 may include nodes arranged in different layers, such as an input layer 410, multiple hidden or intermediary layers 420, and an output layer 430. In some implementations, the number of nodes at the input and output layers may vary from those shown in FIG. 4. Additionally, or alternatively, the number of hidden or intermediate layers, and/or the number of nodes therein, may vary from those shown in FIG. 4.

Example NN 400 may include a number N of inputs introduced to four input nodes [N, 4] of input layer 410. This may include processing or encoding input data into a form, shape, vector, or data structure, that is receivable by the NN. The four input nodes may process the inputs to produce a first weighted value ($W_1$) that the four input nodes provide to five nodes [4;5] of a first hidden layer.

The five nodes of the first hidden layer may use a first function ($f_1$) to process the inputs to produce a second weighted value ($W_2$) that the five nodes of the first hidden layer may provide to the five nodes [5;5] of a second hidden layer. The five nodes of the second layer may use a second function ($f_2$) to process the inputs to produce a third weight ($W_3$) that the five nodes of the second hidden layer may provide to the three nodes [5;3] of output layer 430. The nodes of output layer 430 may each process the inputs received and produce an output. This may include converting or unencoding output data from a form, shape, vector, or data structure, that may be used by a subsequent algorithm, process, or procedure.

As described herein, the techniques described herein may include an integrated NN. In some implementations, the learned features of multiple NNs may be combined to form an integrated NN, by encoding the outputs from other NNs and introducing the encoded outputs into a hidden or intermediate layer of the integrated NN. For example, in some implementations, the integrated NN may be an image analysis NN that is modified or augmented by the incorporation of encoded outputs of other (non-image) NNs.

Artificial intelligence (AI) may involve the combination of computer science and datasets to enable problem-solving. AI may encompass machine learning (ML) and deep learning (DL). These disciplines may comprise of AI or NN algorithms designed to create expert systems which make predictions or classifications based on input data. NNs may be a type of DL algorithm, and DL may be a sub-field of ML. DL and ML algorithms may differ in how each type of algorithm learns. Deep ML may use labeled datasets (also known as supervised learning) to inform its algorithm, but Deep ML does not necessarily require a labeled dataset. DL may ingest unstructured data in its raw form (e.g., text or images) and may automatically determine the set of features which distinguish different categories of data from one another. This may eliminate some of the human intervention required and enable use of larger data sets.

NNs or artificial NNs (ANNs) may comprise logically interconnected nodes arranged in node layers. There may be an input layer, one or more hidden or intermediate layers, and an output layer. Each node, or artificial neuron, may connect to another and has an associated weight and threshold. If the output of any individual node is above the specified threshold value, that node may be activated, sending data to the next layer of the network. Otherwise, no data may be passed along to the next layer of the network by that node. The "deep" in DL may refer to the number of layers in a NN. A NN that consists of more than three layers—which would be inclusive of the input and the output—can be considered a deep learning algorithm or a deep NN.

Feedforward NNs may include an input layer, one or more hidden layers, and an output layer. One type of feedforward NN, referred to as a multi-layer perceptron (MLP), may be one where all, or multiple, layers of the NN are fully connected, meaning that each layer that feeds into the next layer connects to all nodes in the next layer. These networks may learn from input data and may function as a foundation for computer vision, natural language processing, and other neural networks. Recurrent neural networks (RNNs) may be identified by feedback loops. Convolutional NNs (CNNs) may be similar to MLPs, but they differ in that not all layers are fully connected and instead have convolutional layers and pooling layers and may be used for image recognition, pattern recognition, and/or computer vision. These NNs may harness principles from linear algebra, particularly matrix multiplication, to identify patterns within an image. Linear regression analysis, for example, may be used to predict a value of a variable based on a value of another variable. This form of analysis may estimate coefficients of a linear equation, involving one or more independent variables that best predict the value of the dependent variable. Linear regression may fit a straight line or surface that minimizes discrepancies between a predicted value and an actual value. These learning algorithms may be leveraged when using time-series data to make predictions about future outcomes.

Generally, a patient biopsy sample may be cut into thin slices and mounted on glass or otherwise transparent slides. Each slide may include a complete image of the corresponding biopsy slice. Each slide may be captured as an image that supports many levels of zoom (e.g., 80×) that may enable a doctor or image analysis NN to inspect and analyze features of each slide at varying microscopic levels. A doctor, physician, medical technician, or another type of medical professional may analyze the slides for features of concern (e.g., indications of melanoma) and may create clinical notes based on the analysis. The physical slides may be digitized by capturing the slides with a camera, and/or other type of image capturing device, and storing the captured image data as digital information. The physical slides may be submitted for molecular testing, which may include extracting DNA or RNA from the samples and testing the DNA or RNA for certain biomarkers. In some implementations, a polymerase chain reaction (PCR) test and machine may be used; however, other DNA or RNA extraction and/or analysis procedures may also be used. A PCR test may duplicate DNA or RNA many times, after conversion to complementary DNA (cDNA) and/or may identify DNA or RNA sequences of interest (e.g., sequences indicative of a tumor and/or characteristics of the tumor). The PCR test may also, or alternatively, analyze sequences of interest and/or output data (e.g., an output vector) indicating the presence of one or more biomarkers consistent with a tumor. A biomarker, as described herein, may include a sequence of DNA or RNA, and/or a combination of DNA or RNA sequences, identified as being associated with or indicative of melanoma. The results of the PCR test (and/or one or more other types of genetic tests applied consistent with the techniques described herein) may be digitized and sent to pathology servers 220, and pathology servers 220 may process the genetic testing results into molecular input data (e.g., process the genetic test results for application as input data into a molecular analysis NN).

Training image analysis NN, according to one or more of the techniques described herein, may include a combination of supervised, unsupervised, and semi-supervised training. With supervised training, a physician or other medical professional may annotate a set of training data that comprises edges of a tumor, blood vessel, an area of dermis or epidermis, or another specific structure that is extracted by the physician. The known structure is then digitized as image data and used as training data. Supervised learning may provide the NN with an annotated dataset that is extremely accurate but also demonstrates low diversity because of the time and effort required to extract such samples.

The lack of diversity resulting from supervised training may be offset by applying semi-supervised training. With semi-supervised training, the image analysis NN may initially be trained on a supervised dataset and subsequently make predictions on an unannotated dataset in order to generate new data points for further training. The image analysis NN's predictions may be categorized into examples of true positives, true negatives, false positives and false negatives which collectively may be used as data for additional training. Thus, a combination of supervised and semi-supervised training may be implemented to achieve training data that covers a broad range of data points leading to a more generalizable and accurate model. The image analysis NN may include a random forest algorithm. The random forest algorithm may include an ensemble learning method for classification, regression and other tasks that operate by constructing multiple decision trees during NN training.

Additionally, the integrated NN may be configured to implement a cross-attention technique to distinguish between features or characteristics that are important, unimportant or redundant for purposes of pathology. For example, a particular molecular sequence may cause a specific image feature to appear in all cases. In such a scenario, pathology servers 220 may determine that the molecular sequence and corresponding image feature are redundant and may therefore update the learned features of the integrated NN so that predictive weight is only given to either the molecular sequence or the set of features and not both. Similarly, pathology servers 220 may update the learned weights of the integrated NN when a feature or characteristic is determined to be unimportant.

Figure 5:
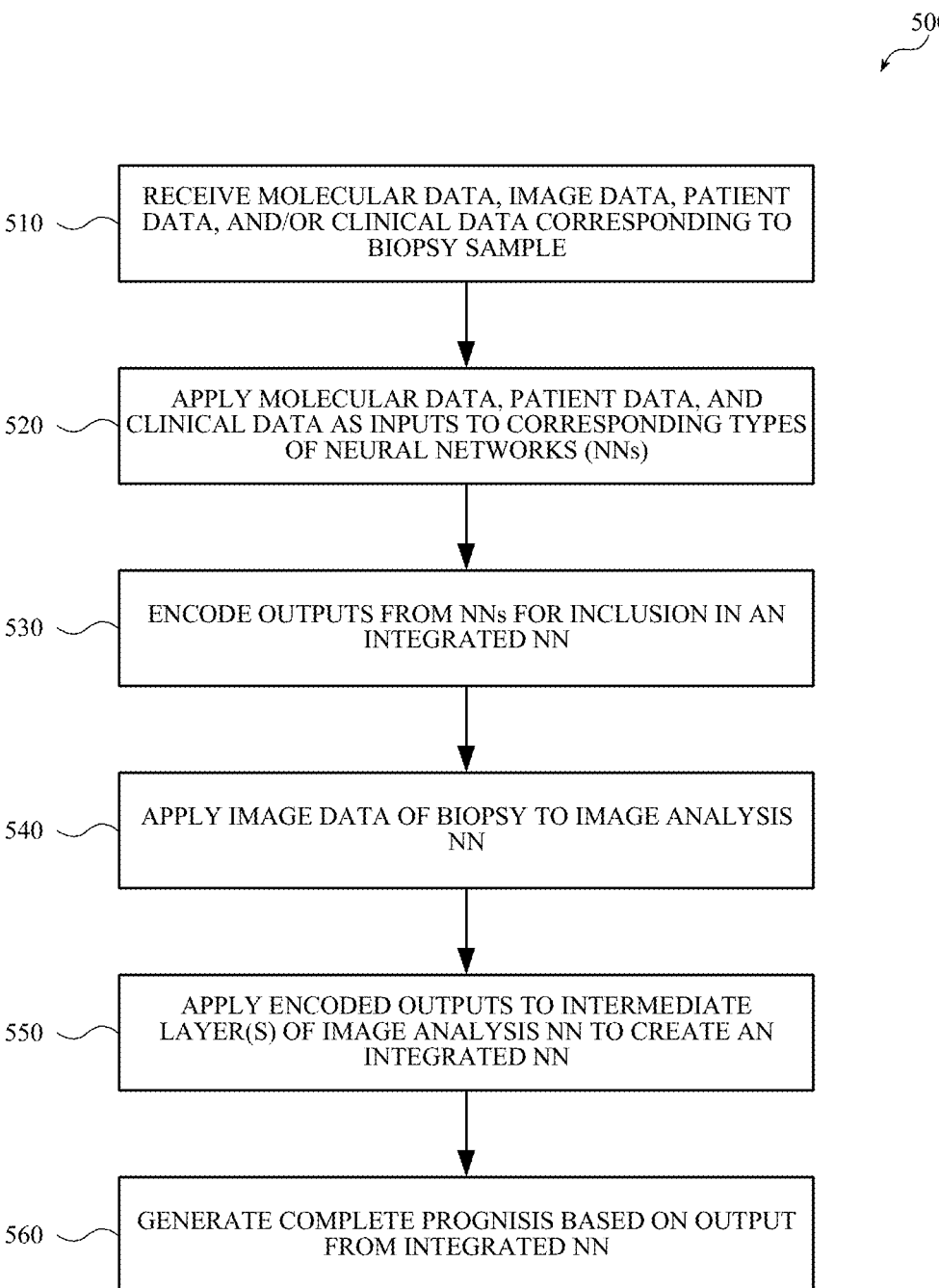
FIG. 5 is a diagram of an example of a process for using multiple data types and NNs to generate a complete prognosis for a melanoma patient and biopsy sample according to one or more implementations described herein.

FIG. 5 is a diagram of an example of a process for using multiple data types and NNs to generate a complete prognosis for a melanoma patient and biopsy sample according to one or more implementations described herein. Process 500 may be implemented by pathology analysis servers 220. In some implementations, some or all of process 500 may be performed by one or more other systems or devices, including one or more of the devices of FIG. 1. Additionally, process 500 may include one or more fewer, additional, differently ordered and/or arranged operations than those shown in FIG. 5, including other processes and/or operations discussed herein. For example, process 500 may include operations preceding, performed in parallel with, and/or following one or more of the depicted operations. Furthermore, some or all of the operations of process 500 may be performed independently, successively, simultaneously, etc., of one or more of the other operations of process 500. As such, the techniques described herein are not limited to a number, sequence, arrangement, timing, etc., of the operations or process depicted in FIG. 5.

As shown, process 500 may include receiving molecular data, image data, patient data, and/or clinical data corresponding to a biopsy (block 510). For example, pathology servers 220 may receive molecular data, image data, patient data, and/or clinical data for a biopsy sample and/or corresponding patient. The molecular data may be an output from a PCR machine or another type of molecular analysis system. The image data may be digitalized image slides of the biopsy sample. The patient data may be information received from a centralized repository (e.g., data entry source 240) and/or submitted to pathology servers 220 along with the molecular data, image data, etc. Clinical data may be information about the biopsy sample and/or patient submitted via doctor office terminal 210.

Process 500 may include applying molecular data, patient data, and clinical data as inputs to corresponding types of NNs (block 520). For example, pathology servers 220 may apply the molecular data, patient data, and clinical data, corresponding to a biopsy sample and/or patient, to a corresponding set of NNs. For instance, pathology servers 220 may include various types of NNs. Some of the NNs may be configured to analyze molecular data; some of the NNs may be configured to analyze patient data, and some NNs may be configured to analyze clinical data. In some implementations, a single NN may be configured to analyze a combination of patient data and clinical data.

Process 500 may include encoding outputs from NNs for inclusion in an integrated NN (block 530). For example, pathology servers 220 may be configured to encode the outputs from a molecular analysis NN, a patient data analysis NN, and/or a clinical notes analysis NN for inclusion into an integrated NN. As described herein, the integrated NN may be an image analysis NN modified by the output of one or more NNs (e.g., an output of the molecular analysis NN, patient data analysis NN, and clinical notes analysis NN). Encoding an output of a NN for inclusion into another NN may involve: determining a weight or significance of the output relative to an overall predictive goal of the other NN; generating a data structure that represents the significance of the output and is applicable to an intermediate layer of the other NN; and modifying the intermediate layer of the other NN with the data structure derived from the output.

For example, pathology servers 220 may apply molecular data to a molecular analysis NN to produce a prediction of future melanoma metastasis based on an output of the molecular analysis NN. Pathology servers 220 may evaluate a strength or weight of the output based on the direct prediction provided by the molecular analysis NN and/or the significance or weight of molecular data relative to other types of data and NN analyses. Further, pathology servers 220 may encode the output of the molecular analysis NN so that the output may be applied to an image analysis NN. Encoding the output of the molecular analysis NN may include generating a data structure that represents the strength of the molecular analysis output and that may be incorporated into one or more intermediate layers of the image analysis NN. Thus, encoding the output of one type of NN to be complementary to another type of NN may include generating a data set that may be incorporated into one or more intermediate layers of a different (and/or a different type) of NN.

Process 500 may also include applying image data of a biopsy to an image analysis NN (block 540). For example, pathology servers 220 may be configured to submit image data of a biopsy to an image analysis NN. The image analysis NN may be configured to analyze image data in the form of individual patches of a fixed resolution (e.g., 64×64 pixel patches, 128×128 pixel patches, etc.) for features or other indications of a melanoma. Examples of such features or indications may include pixels arranged in one or more patterns (e.g., size, shape, color, etc.) and/or the presence of one or more patterns. The image analysis NN may further be configured to determine regions of interest (ROI) by analyzing the pixels and patterns identified among multiple image patches of a given biopsy sample. An example of an ROI may include features and patterns indicative of a nucleus of a tumor. Once identified, ROIs may be further analyzed by the image analysis NN by creating and analyzing smaller patches of the ROI (e.g., 16×16 pixels, 32×32 pixels, etc.) at a greater degree of magnification (e.g., 80× magnification). Doing so may enable the identification and evaluation of specific features and sub-features of the ROI. Additionally, applying such a tiered approach to analyzing image data may increase efficiency without forfeiting accuracy by first identifying ROIs and then closely analyzing ROIs.

In some implementations, the image analysis NN may include a vision transformer (ViT) NN. In some implementations, the image analysis NN may include a graph convolutional NN (GCNN). A ViT NN, GCNN, or another type of NN may be capable of representing relations or edges between a collection of entities or nodes which may help in predicting growth patterns of one or more tumor cells based on the cell neighboring environment and other certain dependencies. A ViT NN or a GCNN may enable the determination and evaluation of relationships between tumor cells and non-tumor cells (e.g., blood vessels, lymphocytes, etc.). Doing so may enable the image analysis NN to predict future growth patterns and trajectories of tumor cells, such as how and in which directions tumor cells may be likely to grow because of nearby non-tumor cells, and a degree of danger presented by such growth. For example, the image analysis NN may be capable of predicting how fast and which directions a tumor may grow and whether the tumor is likely to grow toward lymphocytes. The image analysis may also reveal that certain protective structures have been destroyed by the tumor or inflammation.

In some implementations, the image analysis NN may be configured to evaluate a biopsy sample based on adnexal structures. An adnexal structure may include physical features of a patient's body that may impact the growth and aggressiveness of a tumor based on whether the structure is still intact. An example of an adnexal structure may be a hair follicle. A hair follicle that has been compromised by a tumor may enable the tumor to spread throughout the body more rapidly. The image analysis NN may use a ViT NN or a GCNN to analyze and evaluate adnexal structures.

Process 500 may include applying encoding outputs to one or more intermediate layers of the image analysis NN (block 550). For example, pathology servers 220 may be configured to apply encoded outputs from other NNs to one or more intermediate layers of the image analysis NN. A strong indication from the output of the molecular analysis NN may increase the probabilistic strength of an output of the image analysis NN being predictive of future melanoma metastasis, whereas a weak indication from the output of the molecular analysis NN may decrease the probabilistic strength of the output being predictive of future melanoma metastasis. Pathology servers 220 may be configured to evaluate and apply the outputs of the patient data analysis NN and/or the clinical notes analysis NN in a similar fashion. The intermediate layer selected for including output data from other NNs may be a pooling layer or a penultimate layer of the NN. This intermediate layer may produce a single vector and the outputs of other NNs may be encoded and included as part of, or a feature of, the single vectors at the intermediate layer of the NN. Applying encoded outputs of other NNs to the intermediate layers of the image analysis NN may fundamentally alter the nodes of the intermediate layers and thereby create an integrated NN as described herein.

Process 500 may include generating a complete prognosis based on the output from the integrated NN (block 560). For example, pathology servers 220 may be configured to generate a prognosis based on the output from the integrated NN. The prognosis may be a complete prognosis since the output of the integrated NN may include a complete AI evaluation of patient and biopsy data.

Figure 6:
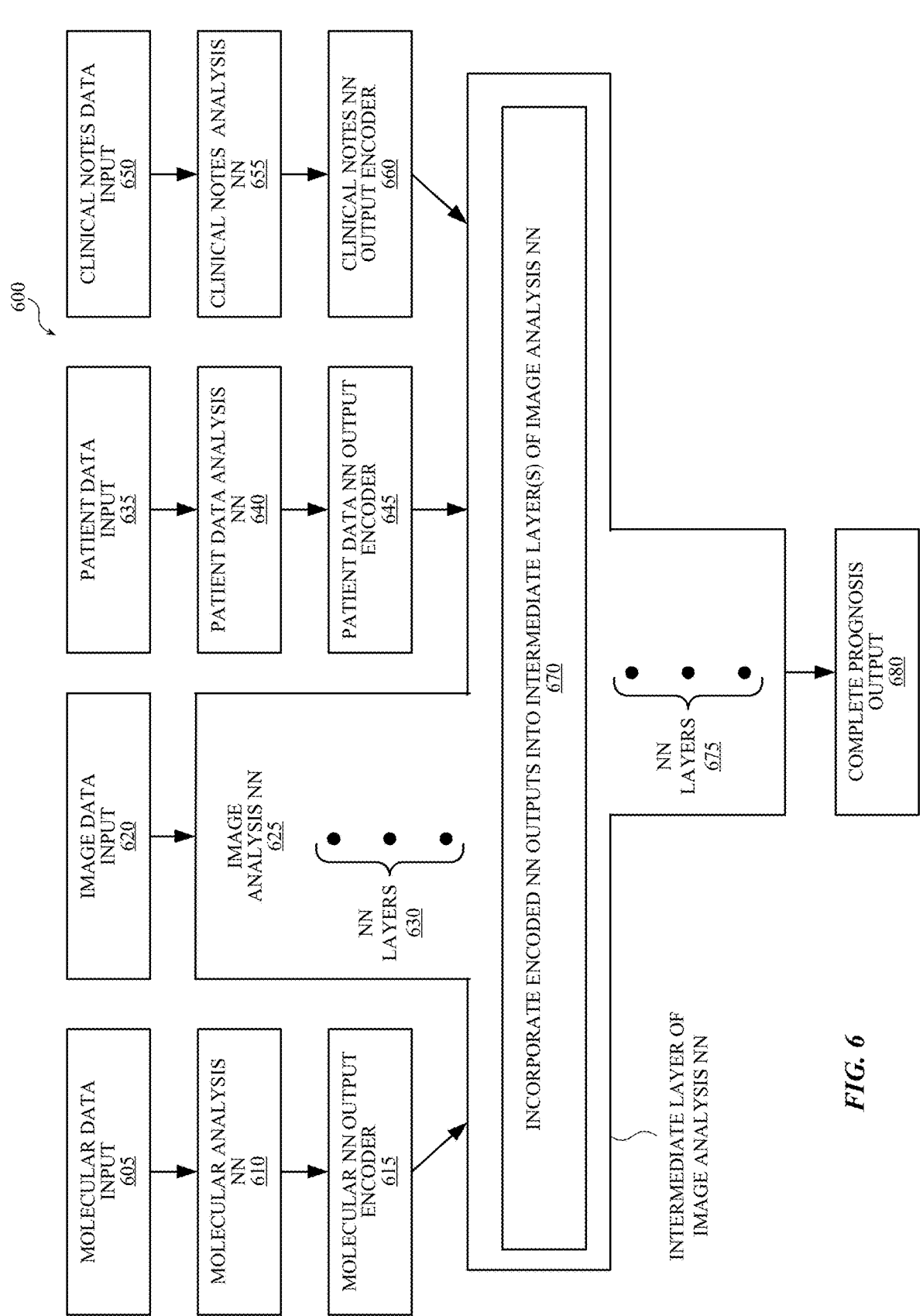
FIG. 6 is a diagram of an example of integrating NNs to produce a complete prognosis output according to one or more implementations described herein.

FIG. 6 is a diagram of an example 600 for melanoma pathology based on integrated NNs according to one or more implementations described herein. As shown, example 600 may include several entities, such as molecular data input 605, molecular analysis NN 610, molecular NN output encoder 615, image data input 620, image analysis NN 625, patient data input 635, patient data analysis NN 640, patient data NN output encoder 645, clinical notes input 650, clinical notes analysis NN, clinical notes output encoder 660, and complete prognosis output 680, Image analysis 625 may include NN layers 630 and 675. The entities of example 605 may be implemented by pathology servers 220. In some implementations, example 605 may include fewer, additional, alternative, and/or differently arranged entities. Example 600 is described below with reference to FIGS. 7-9.

Pathology servers 220 may receive molecular data input 605, image data input 620, patient data input 635, and clinical notes input 650. Molecular data input 605 may include genetic information corresponding to a biopsy sample. Molecular data input 605 may including information produced by a PCR machine or other type of genetic testing device. Molecular data input 605 may be applied to molecular analysis NN 610, which may be a 1-dimensional convolutional NN (CNN) with a data shape of [batch_size, N_features]. Molecular analysis NN 610 may be configured to identify and analyze molecular data inputs 605 for one or more pre-selected biomarkers.

Figure 7:
FIG. 7 is a figure of an example of biomarkers according to one or more implementations described herein.

FIG. 7 is a figure of an example of biomarkers 700 according to one or more implementations described herein. As shown, biomarkers may include one or more genetic sequences, such as TOR1AIP1, BAP1, MGP, SPP1, CXCL14, CLCA2, S100A8, BTG1, SAP130, ARG1, KRT6B, GJA1, ID2, EIF1B, S100A9, CRABP2s, KRT14, ROBO1, RBM23, TACSTD2, DSC1, SPRR1B, TRIM29, AQP3, TYRP1, PPL, LTA4H, and CST6. In some implementations, molecular analysis NN 610 may be trained or configured to analyze molecular input data 605 for biomarkers 700. In some implementations, additional, alternative, fewer, or different biomarkers may be used by molecular analysis NN 610.

Referring to FIG. 6, molecular NN output encoder 615 may be configured to receive output data from molecular analysis NN 610 and encode the output for inclusion or incorporation into image analysis NN 625. The encoded output data may include a feature vector with a shape of [batch_size, N_features], where batch_size is the number of set of molecular data points being analyzed and N_features is the number of features contained in each feature vector for each specific molecular data point. In some implementations, encoded molecular output information may be concatenated, or added to, other types of encoded data such as encoded image data, encoded patient data, and encoded clinical data.

Patient data input 635 and clinical notes data input 650 may include information about the patient (e.g., gender, age, lifestyle, medical history, etc.) and notations about the patient and/or biopsy sample added by a physician or other medical professional. Patient data input 635 and clinical notes data input 650 may be received from doctor office terminals 210 and/or one or more data entry sources 240. Patient data input 635 and clinical notes data input 650 may be applied to patient data analysis NN 640 and clinical notes analysis NN 655, respectively, which may each be a CNN. In some implementations, patient data input 635 clinical notes data input 650 may be received together and/or applied to a single NN.

FIG. 8 is a diagram of an example of patient data and clinical notes data 800 according to one or more implementations described herein. As shown, patient data and clinical notes data 800 may include a date of birth, age at diagnosis, gender, Fitzpatrick skin color, Breslow thickness, ulcerations, mitotic rate, node status, an American Joint Committee on Cancer (AJCC) stage, T stage, date of biopsy of primary melanoma, location of primary tumor, and more. In some implementations, patient data and clinical notes data 800 may include additional, alternative, fewer, or different information than that shown in FIG. 8.

Referring to FIG. 6, patient data NN output encoder 645 and clinical notes NN output encoder 660 may be configured to receive and encode output data from patient data analysis NN 640 and clinical notes analysis NN 655. The encoded output data may include a feature vector with a shape of [batch_size, N_features], where batch_size is the number of set of patient data points being analyzed and N_features is the number of features contained in each feature vector for each specific patient data point.

Figure 9:
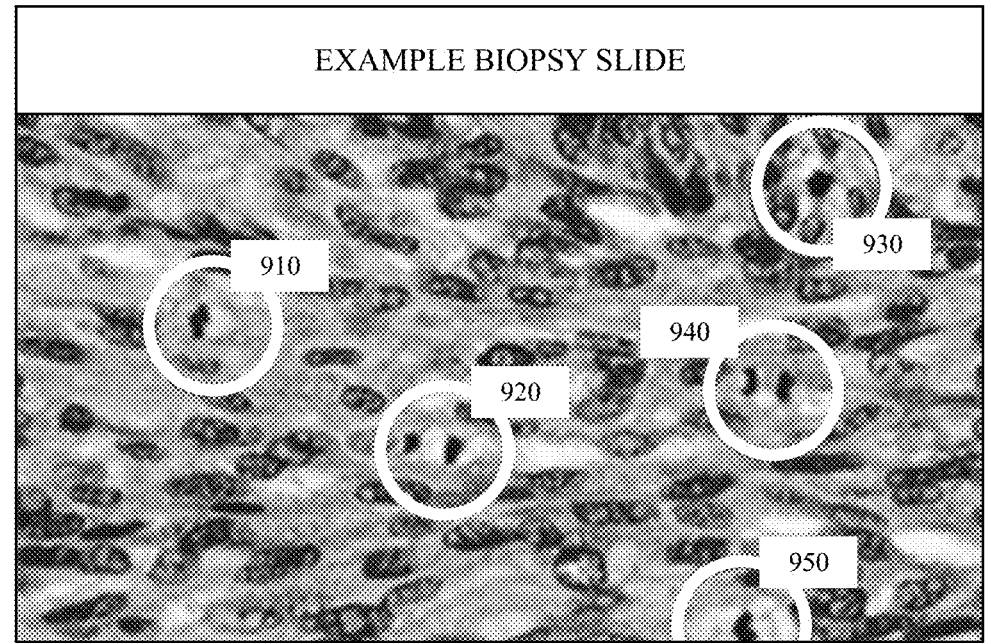
FIG. 9 is a diagram of an example of a biopsy slide according to one or more implementations described herein.

Image input data 620 may be derived from slides produced from a sample biopsy. FIG. 9 is a diagram of an example of a biopsy slide 900 according to one or more implementations described herein. As shown, example slide 900 includes several features 910, 920, 930, 940, and 950, which may be indicative with melanoma, and surrounding biological tissue and structures.

Referring to FIG. 6, image input data 620 may be applied to an input layer of image analysis NN 625, which may include a CNN or ViT NN or GCNN or similar NN which is suited for analyzing data of shape [batch-size, H, W, C], where batch_size is the number of image data points being analyzed, H is image height measured in pixels, W is image width measured in pixels, and C is the number of channels represented in the image, typically 3 for red, green, and blue color channels. Image analysis NN 625 may include one or more intermediate layers 630 and 675 before and after the intermediate layer(s) 760 to which the encoded molecular data, patient data, and clinical notes data are applied. An intermediate layer output of image analysis NN 625 may be a feature vector with a data shape of [batch_size, N_features]. Since encoded outputs from molecular NN output encoder 615, patient data NN output encoder 645, and clinical notes output encoder 660 may each have a data shape of [batch_size, N_features], and since an output of an intermediate layer of image analysis NN 625 may each have a data shape of [batch_size, N_features], the output data outputs from molecular NN output encoder 615, patient data NN output encoder 645, and clinical notes output encoder 660 may be concatenated or applied the intermediate output layer of image analysis NN 625.

After including or concatenating the encoded output data into intermediate layer 670, image analysis NN 625 may proceed to generate a complete prognosis output 680 based on a combination of molecular data, image data, patient data, and clinical notes data. For example, the combined feature vector may be passed through a final classifier layer (dense layer) of image analysis NN 625 followed by an activation function such as a Sigmoid or Softmax function, to generate a prediction which represents the prognosis output. Complete prognosis output 680 may be predictive or infer information about the likelihood and level of risk of metastasis for the melanoma found in the patient sample.

In some implementations, molecular analysis NN 605 may be pretrained individually on molecular data. Image analysis NN 625, patient data analysis NN 640, and clinical notes analysis NN 655 may each be similarly pre-trained based on the data type (image, patient data, etc.) of the corresponding NN. Image analysis NN 625 may be modified, as described above, such that, for example, for each batch of image training data, encoded molecular data, encoded patient data, and/or encoded clinical notes data may be concatenated therewith. A classifier layer (e.g., a dense layer) of image analysis NN 625 may be modified to take concatenated features as input and output a prognostic prediction. The modified image analysis NN may be referred to herein as an integrated NN as it combines the learned features and weightings of multiple different modality-driven NNs into an overall AI-driven function.

Figure 10:
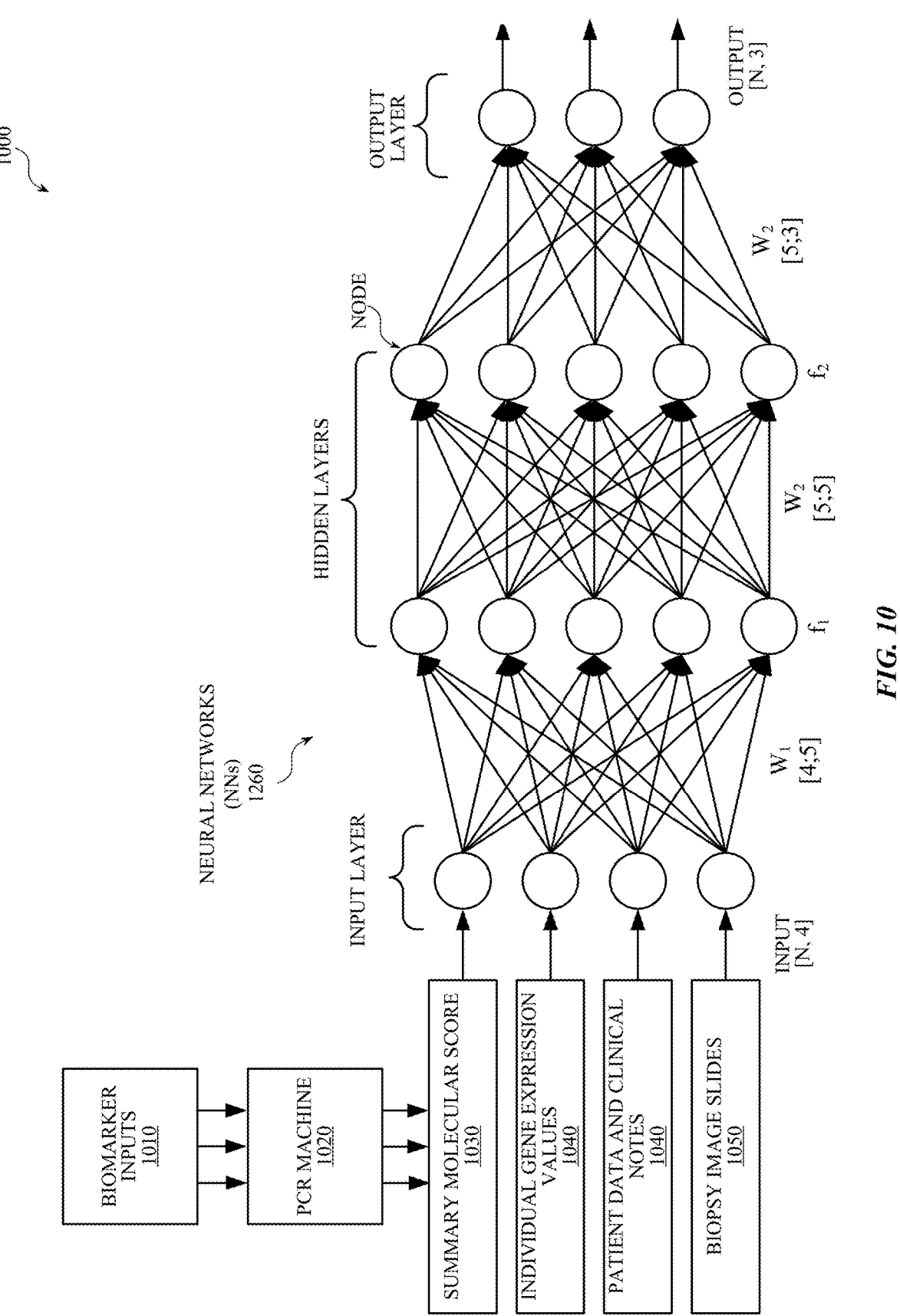
FIG. 10 is a diagram of an example NN for melanoma pathology according to one or more implementations described herein.

FIG. 10 is a diagram of an example 1000 for melanoma pathology according to one or more implementations described herein. As shown, FIG. 10 may include bio marker inputs 1010, PCR machine 1020, summary molecular score 1030, individual gene expression values 1040, patient data and clinical notes 1040, biopsy image slides 1050, and NNs 1260. Example 1000 is provided as a non-limiting example of one or more of the implementation described herein. In other implementations, example 1000 may include one or more additional elements or features, alternative elements or features, and/or differently arranged elements or features than those depicted in FIG. 10.

Biomarker inputs 1010 may include genetic sequences or genes that may be targeted by PCR machine 1020. A non-limiting example of biomarkers that may be targeted by PCR machine 1020 are discussed above with reference to FIG. 7. PCR machine 1020 may receive a biopsy sample and determine whether the genetic material of the biopsy sample include one or more of biomarker inputs 1010. Based on the extent to which the biomarkers are found in the biopsy sample, a summary molecular score 1030 may be derived. Generally, as the number of biomarkers found in the biopsy sample increases, summary molecular score 1030 may increase as well. In some implementations, the presence of certain biomarkers, certain concentration ratios of different biomarkers, and/or groups of biomarkers may affect summary molecular score 1030 more than others.

Individual gene expression values 1040 may include calculated Delta Quantification Cycle ($\Delta C_q$) values that are calculated by subtracting the mean Quantification Cycle (Cq) value from each biomarker gene from the mean of the $C_q$ values obtained from the endogenous control gene(s). Patient data and clinical notes 1040 and biopsy image slides 1050 are discussed above with reference to preceding Figures. The depicted features of NNs 1260 are also discussed above with reference to FIG. 4. Summary molecular score 1030, individual gene expression values 1040, patient data and clinical notes 1040, and biopsy image slides 1050 may be applied as inputs to the input layers of NNs 1260. As described above with reference to, for example, FIGS. 5-6, each NN of NNs 1260 may be data type specific and output of the NNs may be incorporated into an integrated NN.

As such, each of summary molecular score 1030, individual gene expression values 1040, patient data and clinical notes 1040, and biopsy image slides 1050 may be applied to a different type of NN. An output of the NNs for summary molecular score 1030, individual gene expression values 1040, and patient data and clinical notes 1040 may be encoded according to a preselected encoding scheme so that the encoded outputs may be included or applied to a hidden or intermediate layer of the NN applied to biopsy image slides 1050. In so doing, the NN applied to biopsy image slides 1050 may function as an integrated NN to produce an output layer that comprises a complete output that is based on a combination of summary molecular score 1030, individual gene expression values 1040, patient data and clinical notes 1040, and biopsy image slides 1050.

FIG. 11 is a diagram of an example process for melanoma pathology according to one or more implementations described herein. Process 1100 may be implemented by pathology servers 220. In some implementations, some or all of process 1100 may be performed by one or more other systems or devices, including one or more of the devices of FIG. 1. Additionally, process 1100 may include one or more fewer, additional, differently ordered and/or arranged operations than those shown in FIG. 11, including other processes and/or operations discussed herein. For example, process 1100 may include operations preceding, performed in parallel with, and/or following one or more of the depicted operations. Furthermore, some or all of the operations of process 1100 may be performed independently, successively, simultaneously, etc., of one or more of the other operations of process 1100. As such, the techniques described herein are not limited to a number, sequence, arrangement, timing, etc., of the operations or process depicted in FIG. 11.

Process 1100 may include producing AI-generated prognosis image data based on patient sample images (block 1110). For example, prognosis servers 220 may receive digitized images of a slices of a patient biopsy sample and apply the digitized image data to AI tools (e.g., an image analysis NN), and produce a melanoma prognosis based on the output data for the AI tools. Process 110 may also include producing AI-generated prognosis genetic data based on a patient biopsy sample (block 1120). For example, the patient biopsy sample may be subjected to genetic testing (e.g., a PCR test) configured to determine the level of gene expression of one or more biomarkers found in the biopsy sample. Prognosis servers 220 may apply AI tools (e.g., a molecular analysis NN) to the results of the genetic testing to produce a melanoma prognosis for the genetic data.

Process 1100 may include determining AI-generated prognosis patient data based on patient medical records (block 1130). For example, prognosis servers 220 may receive patient data from doctor office terminal 210, data entity source 240, or another type of device. Prognosis servers 220 may apply the patient data to AI tools (e.g., a patient data analysis NN) to produce a melanoma prognosis based on the patient data. In some implementations, process 1100 may also, or alternatively, prognosis servers 220 determining an AI-generated prognosis for melanoma based on clinical notes data.

Process 1100 may also include applying AI tools to a combination of the melanoma prognoses from the image data, genetic data, patient records data, and/or clinical notes data (block 1130). For example, prognosis server 220 may process, format, encode, etc., the melanoma prognoses to be appropriate as inputs into an aggregate NN. The aggregate NN may be configured to analyze a combination of the melanoma prognoses and produce a corresponding complete prognosis output. Process 1100 may include generating a complete prognosis report (block 1140). For example, prognosis servers 220 may be configured to generate a prognosis report based on the complete prognosis output resulting applying the combination of melanoma prognoses to an aggregate NN. The prognosis report may include text, graphics, or other information features presented in a pre-selected format and may be displayed on a screen or printed out on paper.

Process 1100 may include updating AI training data based on prognosis feedback data (block 1150). For example, prognosis servers 220 may receive prognosis feedback data regarding a prognosis output. The prognosis feedback data may include a physician or another medical professional confirming, denying, or correcting a prognosis output of prognosis servers 220. Prognosis servers 220 may apply the prognosis feedback to the prognosis output and incorporate the prognosis output and overall data set to a set of training data used to train one or more of the NNs described above.

Process 1100 may include training AI tools based on updated AI training data (block 1160). For example, prognosis servers 220 may retrain one or more of the NNs described above using a set of training data that has been updated after receiving and applying prognosis feedback. Doing so may enable the updated NN to produce prognoses with a greater and more reliable degree of accuracy.

Figure 12:
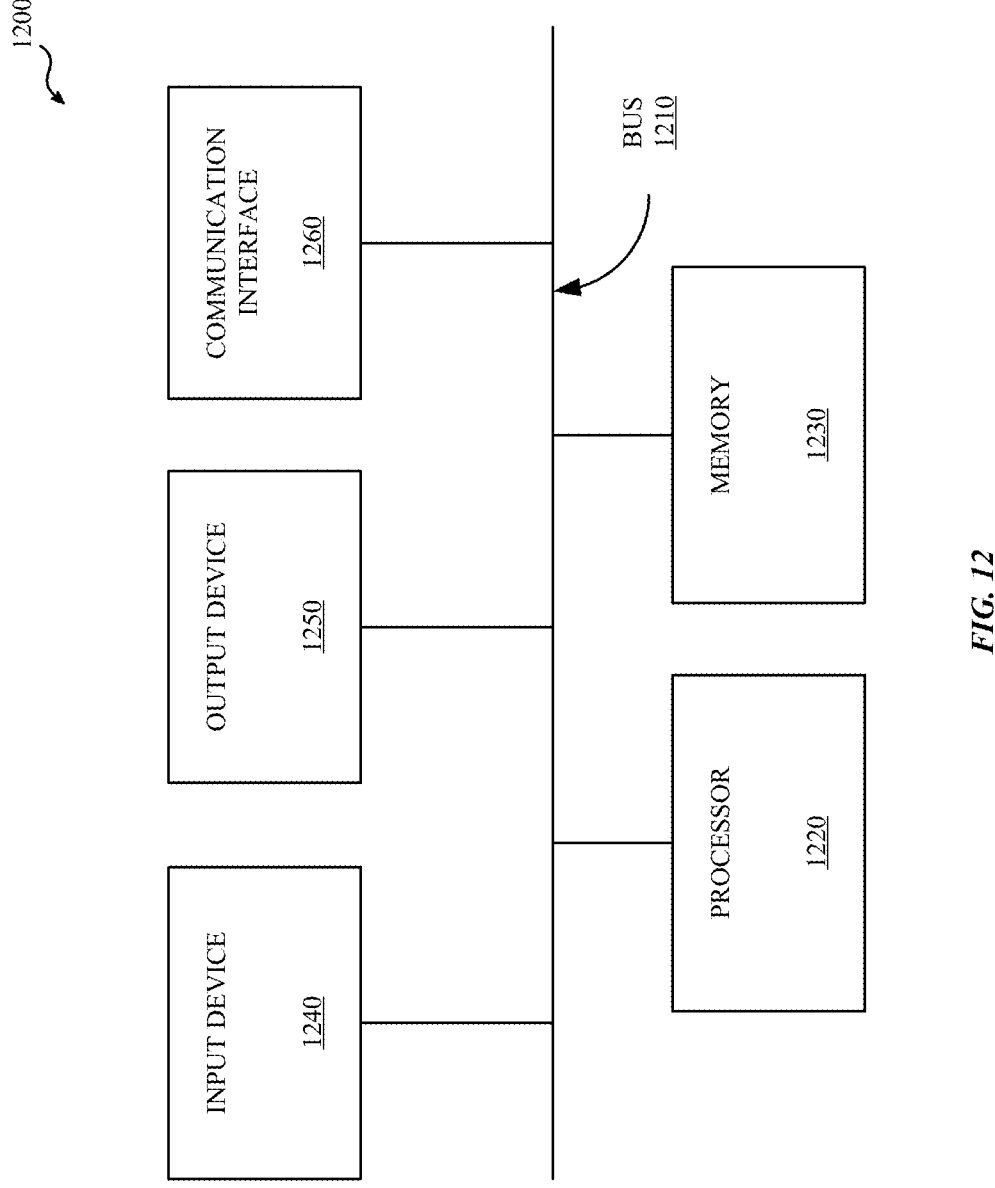
FIG. 12 is a diagram of an example of components of a device according to one or more implementations described herein.

FIG. 12 is a diagram of example components of a device 1200 that may be used within environment 200 of FIG. 2. Device 1200 may correspond to doctor office terminals 210, pathology servers 220, pathology platform management terminal 230, and/or data entry source 240. Each of doctor office terminals 210, pathology servers 220, pathology platform management terminal 230, and/or data entry source 240 may include one or more of devices 1200 and/or one or more of the components of device 1200.

As depicted, device 1200 may include bus 1210, processor 1220, memory 1230, input device 1240, output device 1250, and communication interface 1260. However, the precise components of device 1200 may vary between implementations. For example, depending on the implementation, device 1200 may include fewer components, additional components, different components, or differently arranged components than those illustrated in FIG. 12.

Bus 1210 may permit communication among the components of device 1200. Processor 1220 may include one or more processors, microprocessors, data processors, co-processors, network processors, application-specific integrated circuits (ASICs), controllers, programmable logic devices (PLDs), chipsets, field-programmable gate arrays (FPGAs), or other components that may interpret or execute instructions or data. Processor 1220 may control the overall operation, or a portion thereof, of device 1200, based on, for example, an operating system (not illustrated), and/or various applications. Processor 1220 may access instructions from memory 1230, from other components of device 1200, or from a source external to device 1200 (e.g., a network or another device).

Memory 1230 may include memory and/or secondary storage. For example, memory 1230 may include random access memory (RAM), dynamic RAM (DRAM), read-only memory (ROM), programmable ROM (PROM), flash memory, or some other type of memory. Memory 1230 may include a hard disk (e.g., a magnetic disk, an optical disk, a magneto-optic disk, a solid state disk, etc.) or some other type of computer-readable medium, along with a corresponding drive. A computer-readable medium may be defined as a non-transitory memory device. A memory device may include space within a single physical memory device or spread across multiple physical memory devices.

Input device 1240 may include one or more components that permit a user to input information into device 1200. For example, input device 1240 may include a keypad, a button, a switch, a knob, fingerprint recognition logic, retinal scan logic, a web cam, voice recognition logic, a touchpad, an input port, a microphone, a display, or some other type of input component. Output device 1250 may include one or more components that permit device 1200 to output information to a user. For example, output device 1250 may include a display, light-emitting diodes (LEDs), an output port, a speaker, or some other type of output component.

Communication interface 1260 may include one or more components that permit device 1200 to communicate with other devices or networks. For example, communication interface 1260 may include some type of wireless or wired interface. Communication interface 1260 may also include an antenna (or a set of antennas) that permit wireless communication, such as the transmission and reception of radio frequency (RF) signals.

As described herein, device 1200 may perform certain operations in response to processor 1220 executing software instructions contained in a computer-readable medium, such as memory 1230. The software instructions may be read into memory 1230 from another computer-readable medium or from another device via communication interface 1260. The software instructions contained in memory 1230 may cause processor 1220 to perform one or more processes described herein. Alternatively, hardwired circuitry may be used in place of, or in combination with, software instructions to implement processes described herein. Thus, implementations described herein are not limited to any specific combination of hardware circuitry and software.

Examples herein can include subject matter such as a method, means for performing acts or blocks of the method, at least one machine-readable medium including executable instructions that, when performed by a machine (e.g., a processor (e.g., processor, etc.) with memory, an application-specific integrated circuit (ASIC), a field programmable gate array (FPGA), or the like) cause the machine to perform acts of the method or of an apparatus or system for concurrent communication using multiple communication technologies according to implementations and examples described.

In example 1, which may also include one or more of the examples described herein, a server device may comprise: a memory configured to store instructions; and one or more processors configured to, when executing the instructions stored in the memory, cause the server device to: receive molecular information corresponding to a patient biopsy sample; apply the molecular information to a molecular neural network (NN); produce, based on the molecular information and the molecular NN, molecular output information; generate encoded molecular information by encoding the molecular output information according to a preselected encoding scheme; receive image information corresponding to the patient biopsy sample; apply the image information to an image analysis NN; concatenate the encoded molecular information to the image information at an intermediate layer of the image analysis NN; and produce, based on the encoded molecular information and the image information concatenated at the intermediate layer, a prognosis output from the image analysis NN.

In example 2, which may also include one or more of the examples described herein, the preselected encoding scheme comprises a feature vector comprising a data shape of the image information at the intermediate layer of the image analysis NN. In example 3, which may also include one or more of the examples described herein, the patient biopsy sample comprises a patient skin sample. In example 4, which may also include one or more of the examples described herein, the prognosis output includes at least one of: a recommendation for conducting a nearest node biopsy, a likelihood of metastasis, or a likelihood of recurrence of the melanoma.

In example 5, which may also include one or more of the examples described herein, the molecular output information comprises an indication of melanoma, and concatenation of the encoded molecular information to the image information comprises modifying, in accordance with the encoded molecular information, a feature vector of the image analysis NN at the intermediate layer. In example 6, which may also include one or more of the examples described herein, the molecular information comprises a first data shape, the image information comprises a second data shape that is different from the first data shape, and the encoded molecular information concatenated to the image information at the intermediate layer of the image analysis NN comprises a third data shape that is different from the first data shape and the second data shape.

In example 7, which may also include one or more of the examples described herein, the molecular NN comprises a one-dimensional NN, and the image analysis NN comprises a multi-dimensional convolutional NN (CNN). In example 8, which may also include one or more of the examples described herein, the molecular information comprises a number of molecular features corresponding to a polymerase chain reaction (PCR) procedure of the patient biopsy sample. In example 9, which may also include one or more of the examples described herein, the molecular NN comprises a NN trained using molecular information from a plurality of patient biopsy samples. In example 10, which may also include one or more of the examples described herein, the encoded molecular information comprises a batch size and a number of molecular features of the patient biopsy sample.

In example 11, which may also include one or more of the examples described herein, the image information comprises a batch size and a height (H), weight (W), and color (C) of the patient biopsy sample. In example 12, which may also include one or more of the examples described herein, each slide of the plurality of slides comprises a batch size and image features. In example 13, which may also include one or more of the examples described herein, the image analysis NN comprises a NN trained using image information of a plurality of patient biopsy samples.

In example 14, which may also include one or more of the examples described herein, a data shape of the encoded molecular information shares a same rank or dimensionality with a data shape of the image information at the intermediate layer of the image analysis NN. In example 15, which may also include one or more of the examples described herein, the intermediate layer of the image analysis NN comprises a pooling layer of a convolutional neural network (CNN). In example 16, which may also include one or more of the examples described herein, the image analysis NN comprises a random forest algorithm.

In example 17, which may also include one or more of the examples described herein, the one or more processors are further to cause the server device to: receive patient information corresponding to the patient biopsy sample; apply the patient information to a patient information NN; produce, based on the patient information and the patient information NN, patient output information; generate encoded patient information by encoding the patient output information according to the preselected encoding scheme; and concatenate the encoded patient information to the encoded molecular information and the image information at the intermediate layer of the image analysis NN.

In example 18, which may also include one or more of the examples described herein, the patient output information comprises an indication of a likelihood of metastasis of melanoma, and concatenation of the encoded patient information to the image information comprises modifying, in accordance with the encoded patient information, a feature vector of the image analysis NN at the intermediate layer. In example 19, which may also include one or more of the examples described herein, the molecular information comprises deoxyribonucleic acid (DNA) or ribonucleic acid (RNA) of the patient biopsy sample, the image information comprises a plurality of whole slide images (WSI) of the patient biopsy sample, and the patient information comprises electronic medical records of a patient corresponding to the patient biopsy sample.

In example 20, which may also include one or more of the examples described herein, the one or more processors are further to cause the server device to: receive clinical note information corresponding to the patient biopsy sample; apply the clinical note information to a clinical note NN; produce, based on the clinical note information and the clinical note NN, clinical note output information; generate encoded clinical note information by encoding the clinical note output information according to the preselected encoding scheme; and concatenate the encoded clinical note information to the encoded molecular information and the image information at the intermediate layer of the image analysis NN.

In example 21, which may also include one or more of the examples described herein, the clinical note output information comprises an indication of a likelihood of metastasis of melanoma, and concatenation of the encoded clinical note information to the image information comprises modifying, in accordance with the encoded clinical note information, a feature vector of the image analysis NN at the intermediate layer. In example 22, which may also include one or more of the examples described herein, the molecular information comprises deoxyribonucleic acid (DNA) or ribonucleic acid (RNA) of the patient biopsy sample, the image information comprises a plurality of whole slide images (WSI) of the patient biopsy sample, and the clinical note information comprises physician analysis information of the patient biopsy sample.

In example 23, which may also include one or more of the examples described herein, a method may comprise: receiving molecular information corresponding to a patient biopsy sample; applying the molecular information to a molecular neural network (NN); producing, based on the molecular information and the molecular NN, molecular output information; generating encoded molecular information by encoding the molecular output information according to a preselected encoding scheme; receiving image information corresponding to the patient biopsy sample; applying the image information to an image analysis NN; concatenating the encoded molecular information to the image information at an intermediate layer of the image analysis NN; and producing, based on the encoded molecular information and the image information concatenated at the intermediate layer, a prognosis output from the image analysis NN.

In example 24, which may also include one or more of the examples described herein, the preselected encoding scheme comprises a feature vector comprising a data shape of the image information at the intermediate layer of the image analysis NN. In example 25, which may also include one or more of the examples described herein, the patient biopsy sample comprises a patient skin sample and the prognosis output comprises an indication of a risk level of metastasis of melanoma. In example 26, which may also include one or more of the examples described herein, the molecular output information comprises an indication of a risk level of metastasis of melanoma in the patient biopsy sample, and concatenation of the encoded molecular information to the image information comprises modifying, in accordance with the encoded molecular information, a feature vector of the image analysis NN at the intermediate layer.

In example 27, which may also include one or more of the examples described herein, the molecular NN comprises a one-dimensional NN, and the image analysis NN comprises a multi-dimensional convolutional NN (CNN). In example 28, which may also include one or more of the examples described herein, a method may comprise receiving patient information corresponding to the patient biopsy sample; applying the patient information to a patient information NN; producing, based on the patient information and the patient information NN, patient output information; generating encoded patient information by encoding the patient output information according to the preselected encoding scheme; and concatenating the encoded patient information to the encoded molecular information and the image information at the intermediate layer of the image analysis NN.

In example 29, which may also include one or more of the examples described herein, the patient output information comprises an indication of a risk level of metastasis of melanoma in the patient biopsy sample, and concatenation of the encoded patient information to the image information comprises modifying, in accordance with the encoded patient information, a feature vector of the image analysis NN at the intermediate layer. In example 30, which may also include one or more of the examples described herein, a method may comprise receiving clinical note information corresponding to the patient biopsy sample; applying the clinical note information to a clinical note NN; producing, based on the clinical note information and the clinical note NN, clinical note output information; generating encoded clinical note information by encoding the clinical note output information according to the preselected encoding scheme; and concatenating the encoded clinical note information to the encoded molecular information and the image information at the intermediate layer of the image analysis NN.

In example 31, which may also include one or more of the examples described herein, the clinical note output information comprises an indication of a risk level of metastasis of melanoma in the patient biopsy sample, and concatenation of the encoded clinical note information to the image information comprises modifying, in accordance with the encoded clinical note information, a feature vector of the image analysis NN at the intermediate layer. In example 32, which may also include one or more of the examples described herein, a non-transitory, computer-readable medium may comprise: one or more instructions that when performed by one or more processors, cause the one or more processors to: receive molecular information corresponding to a patient biopsy sample; apply the molecular information to a molecular neural network (NN); produce, based on the molecular information and the molecular NN, molecular output information; generate encoded molecular information by encoding the molecular output information according to a preselected encoding scheme; receive image information corresponding to the patient biopsy sample; apply the image information to an image analysis NN; concatenate the encoded molecular information to the image information at an intermediate layer of the image analysis NN; and produce, based on the encoded molecular information and the image information concatenated at the intermediate layer, a prognosis output from the image analysis NN.

In example 33, which may also include one or more of the examples described herein, the preselected encoding scheme comprises a feature vector comprising a data shape of the image information at the intermediate layer of the image analysis NN. In example 34, which may also include one or more of the examples described herein, the patient biopsy sample comprises a patient skin sample and the prognosis output comprises an indication of a risk level of metastasis of melanoma in the patient biopsy sample. In example 35, which may also include one or more of the examples described herein, the molecular output information comprises an indication of a likelihood of metastasis of melanoma in the patient biopsy sample, and concatenation of the encoded molecular information to the image information comprises modifying, in accordance with the encoded molecular information, a feature vector of the image analysis NN at the intermediate layer. In example 36, which may also include one or more of the examples described herein, the molecular NN comprises a one-dimensional NN, and the image analysis NN comprises a multi-dimensional convolutional NN (CNN).

In example 37, which may also include one or more of the examples described herein, the one or more processors are further to: receive patient information corresponding to the patient biopsy sample; apply the patient information to a patient information NN; produce, based on the patient information and the patient information NN, patient output information; generate encoded patient information by encoding the patient output information according to the preselected encoding scheme; and concatenate the encoded patient information to the encoded molecular information and the image information at the intermediate layer of the image analysis NN. In example 38, which may also include one or more of the examples described herein, the patient output information comprises an indication of a risk level of metastasis of melanoma in the patient biopsy sample, and concatenation of the encoded patient information to the image information comprises modifying, in accordance with the encoded patient information, a feature vector of the image analysis NN at the intermediate layer. In example 39, which may also include one or more of the examples described herein, the clinical note output information comprises an indication of a risk level of metastasis of melanoma in the patient biopsy sample, and concatenation of the encoded clinical note information to the image information comprises modifying, in accordance with the encoded clinical note information, a feature vector of the image analysis NN at the intermediate layer.

In example 40, which may also include one or more of the examples described herein, a device may comprise one or more processors configured to: receive molecular information corresponding to a biopsy sample; receive image information corresponding to the biopsy sample; apply the molecular information and the image information to at least one neural network (NN); and produce, based on an output of the at least one NN, a melanoma prognosis for the biopsy sample. In example 41, which may also include one or more of the examples described herein, the molecular information corresponds to results of a polymerase chain reaction (PCR) procedure performed on the biopsy sample.

The above description of illustrated examples, implementations, aspects, etc., of the subject disclosure, including what is described in the Abstract, is not intended to be exhaustive or to limit the disclosed aspects to the precise forms disclosed. While specific examples, implementations, aspects, etc., are described herein for illustrative purposes, various modifications are possible that are considered within the scope of such examples, implementations, aspects, etc., as those skilled in the relevant art can recognize.

In this regard, while the disclosed subject matter has been described in connection with various examples, implementations, aspects, etc., and corresponding Figures, where applicable, it is to be understood that other similar aspects can be used or modifications and additions can be made to the disclosed subject matter for performing the same, similar, alternative, or substitute function of the subject matter without deviating therefrom. Therefore, the disclosed subject matter should not be limited to any single example, implementation, or aspect described herein, but rather should be construed in breadth and scope in accordance with the appended claims below.

In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations. In addition, while a particular feature may have been disclosed with respect to only one of several implementations, such feature may be combined with one or more other features of the other implementations as may be desired and advantageous for any given application.

As used herein, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. Furthermore, to the extent that the terms "including", "includes", "having", "has", "with", or variants thereof are used in either the detailed description or the claims, such terms are intended to be inclusive in a manner similar to the term "comprising." Additionally, in situations wherein one or more numbered items are discussed (e.g., a "first X", a "second X", etc.), in general the one or more numbered items can be distinct, or they can be the same, although in some situations the context may indicate that they are distinct or that they are the same.

It is well understood that the use of personally identifiable information should follow privacy policies and practices that are generally recognized as meeting or exceeding industry or governmental requirements for maintaining the privacy of users. In particular, personally identifiable information data should be managed and handled to minimize risks of unintentional or unauthorized access or use, and the nature of authorized use should be clearly indicated to users.

What is claimed is:

1. A system for melanoma pathology, comprising:
a memory configured to store instructions;
one or more processors;
a server device;
a plurality of data-specific neural networks (NNs), each NN comprising an input layer, one or more intermediate layers, and an output layer;
wherein the input layer comprises a plurality of input nodes for processing or encoding input data into a data shape receivable by the data-specific NN, each input node being configured to process the input data to produce a first weighted value provided to a first intermediate layer of the one or more intermediate layers;
wherein the system is configured to receive a plurality of prognosis inputs as the input data, the plurality of prognosis inputs comprising:
molecular data comprising genetic information, biological markers, and biological information from a patient biopsy sample; image data; patient data; and clinical notes data;
wherein each type of prognosis input of the plurality of prognosis inputs is applied to a data-specific NN of the plurality of data-specific NNs that is trained or modeled according to a corresponding type of information;
wherein outputs of the plurality of data-specific NNs are encoded according to a preselected encoding scheme and produced by the output layer; and
wherein layers of the plurality of data-specific NNs are integrated such that a combined output of the plurality of data-specific NNs is produced by each NN output being concatenated or applied to the one or more intermediate layers to
produce a complete prognosis output from all of the prognosis inputs and the plurality of data-specific NNs.

2. The system of claim 1, wherein the image data is received by an image analysis NN of the plurality of data-specific NNs, and the preselected encoding scheme used by the imagine analysis NN comprises a feature vector comprising a data shape of the image information at the intermediate layer, and wherein the data shape includes a number of set of molecular data points being analyzed, and a number of features contained in each feature vector for each specific molecular data point.

3. The system of claim 1, wherein the patient biopsy sample comprises a patient skin sample.

4. The system of claim 1, wherein the complete prognosis output includes at least one of: an indication of whether the biopsy sample includes melanoma, whether the melanoma is benign or malignant, a recommendation for conducting a nearest node biopsy, a likelihood of metastasis, or a likelihood of recurrence of the melanoma.

5. The system of claim 1, wherein the molecular data comprises a first data shape, the image data comprises a second data shape that is different from the first data shape, and the encoded molecular data concatenated to the image data at the intermediate layer of an image analysis NN comprises a third data shape that is different from the first data shape and the second data shape.

6. The system of claim 5, wherein the molecular data is received by a molecular NN of the plurality of data-specific NNs, and the molecular NN comprises a one-dimensional NN, and the image analysis NN comprises a multi-dimensional convolutional NN (CNN).

7. The system of claim 5, wherein the molecular data comprises a number of molecular features corresponding to a polymerase chain reaction (PCR) procedure of the patient biopsy sample.

8. The system of claim 5, wherein the molecular NN comprises a NN trained using molecular data from a plurality of patient biopsy samples.

9. The system of claim 5, wherein the encoded molecular data comprises a batch size and a number of molecular features of the patient biopsy sample.

10. The system of claim 5, wherein the image data comprises a batch size and a height (H), weight (W), and color (C) of the patient biopsy sample.

11. The system of claim 5, wherein each slide of a plurality of slides from the patient biopsy sample comprises a batch size and image features.

12. The system of claim 5, wherein the image analysis NN comprises a NN trained using image information of a plurality of patient biopsy samples.

13. The system of claim 5, wherein a data shape of the encoded molecular information shares a same rank or dimensionality with a data shape of the image information at the intermediate layer of the image analysis NN.

14. The system of claim 5, wherein the intermediate layer of the image analysis NN comprises a pooling layer of a convolutional neural network (CNN).

15. The system of claim 5, wherein the image analysis NN comprises a random forest algorithm.

16. The system of claim 1, wherein the one or more processors cause the server device to:

receive patient data corresponding to the patient biopsy sample; apply the patient data to a patient information NN;

produce, based on the patient data and the patient information NN, patient output information;

generate encoded patient information by encoding the patient output information according to the preselected encoding scheme; and concatenate the encoded patient information to the encoded molecular information and the image information at the intermediate layer of the image analysis NN.

17. The system of claim 16, wherein the patient output information comprises an indication of a likelihood of metastasis of melanoma, and concatenation of the encoded patient information to the image information comprises modifying, in accordance with the encoded patient information, a feature vector of the image analysis NN at the intermediate layer.

18. The system of claim 16, wherein the molecular data comprises deoxyribonucleic acid (DNA) or ribonucleic acid (RNA) of the patient biopsy sample, the image data comprises a plurality of whole slide images (WSI) of the patient biopsy sample, and the patient data comprises electronic medical records of a patient corresponding to the patient biopsy sample.

19. The system of claim 1, wherein the one or more processors cause the server device to:

receive clinical notes data corresponding to the patient biopsy sample; apply the clinical notes data to a clinical note NN;

produce, based on the clinical notes data and the clinical note NN, clinical note output information;

generate encoded clinical notes data by encoding the clinical note output information according to the preselected encoding scheme; and concatenate the encoded clinical notes data to the encoded molecular information and the image information at the intermediate layer of the image analysis NN.

20. The system of claim 19, wherein the clinical note output information comprises an indication of a likelihood of metastasis of melanoma, and concatenation of the encoded clinical note information to the image information comprises modifying, in accordance with the encoded clinical note information, a feature vector of the image analysis NN at the intermediate layer.

21. The system of claim 19, wherein the molecular data comprises deoxyribonucleic acid (DNA) or ribonucleic acid (RNA) of the patient biopsy sample, the image data comprises a plurality of whole slide images (WSI) of the patient biopsy sample, and the clinical notes data comprises physician analysis information of the patient biopsy sample.

22. A method for melanoma pathology, comprising:

receiving a plurality of prognosis inputs comprising: molecular data comprising genetic information, biological markers, and biological information from a patient biopsy sample; image data; patient data; and clinical notes data;

applying the plurality of prognosis inputs to a plurality of data-specific neural networks (NNs), wherein each type of prognosis input of the plurality of prognosis inputs is applied to a data-specific NN of the plurality of data-specific NNs that is trained or modeled according to a corresponding type of information;

processing the plurality of prognosis inputs as input data into an input layer of the plurality of data-specific NNs;

encoding outputs of the plurality of data-specific NNs according to a preselected encoding scheme;

concatenating the outputs of the plurality of data-specific NNs and applying the outputs to one or more intermediate layers of the plurality of data-specific NNs; and producing a complete prognosis output from all of the prognosis inputs and the plurality of data-specific NNs.

23. The method of claim 22, wherein the image data is received by an image analysis NN of the plurality of data-specific NNs, and the preselected encoding scheme used by the imagine analysis NN comprises a feature vector comprising a data shape of the image information at the intermediate layer, and wherein the data shape includes a number of set of molecular data points being analyzed, and a number of features contained in each feature vector for each specific molecular data point.

24. The method of claim 22, wherein the patient biopsy sample comprises a patient skin sample and the prognosis output comprises an indication of a risk level of metastasis of melanoma.

25. The method of claim 22, wherein
the molecular output information comprises an indication of a risk level of metastasis of melanoma in the patient biopsy sample, and
concatenation of the encoded molecular data to the image data comprises modifying, in accordance with the encoded molecular information, a feature vector of the image analysis NN at the intermediate layer.

26. The method of claim 22, wherein
the molecular NN comprises a one-dimensional NN, and
the image analysis NN comprises a multi-dimensional convolutional NN (CNN).

27. The method of claim 22, further comprising:
receiving patient data corresponding to the patient biopsy sample; applying the patient data to a patient information NN;
producing, based on the patient data and the patient information NN, patient output information;
generating encoded patient data by encoding the patient output information according to the preselected encoding scheme; and
concatenating the encoded patient data to the encoded molecular data and the image data at the intermediate layer of the image analysis NN.

28. The method of claim 27, wherein
the patient output information comprises an indication of a risk level of metastasis of melanoma in the patient biopsy sample, and
concatenation of the encoded patient data to the image data comprises modifying, in accordance with the encoded patient information, a feature vector of the image analysis NN at the intermediate layer.

29. The method of claim 22, further comprising:
receiving clinical note information corresponding to the patient biopsy sample; applying the clinical notes data to a clinical note NN;
producing, based on the clinical note information and the clinical note NN, clinical note output information;
generating encoded clinical notes data by encoding the clinical note output information according to the preselected encoding scheme; and
concatenating the encoded clinical notes data to the encoded molecular data and the image data at the intermediate layer of the image analysis NN.

30. The method of claim 29, wherein
the clinical note output information comprises an indication of a risk level of metastasis of melanoma in the patient biopsy sample, and
concatenation of the encoded clinical notes data to the image data comprises modifying, in accordance with the encoded clinical note information, a feature vector of the image analysis NN at the intermediate layer.

31. A non-transitory, computer-readable medium comprising:
one or more instructions that when performed by one or more processors, cause the one or more processors to:
receive a plurality of prognosis inputs comprising:
molecular data comprising genetic information, biological markers, and biological information from a patient biopsy sample; image data; patient data; and clinical notes data;
apply the plurality of prognosis inputs to a plurality of data-specific neural networks (NNs), wherein each type of prognosis input of the plurality of prognosis inputs is applied to a data-specific NN of the plurality of data-specific NNs that is trained or modeled according to a corresponding type of information;
process the plurality of prognosis inputs as input data into an input layer of the plurality of data-specific NNs;
encode outputs of the plurality of data-specific NNs according to a preselected encoding scheme;
concatenate the outputs of the plurality of data-specific NNs and applying the outputs to one or more intermediate layers of the plurality of data-specific NNs; and
produce a complete prognosis output from all of the prognosis inputs and the plurality of data-specific NNs.

32. The non-transitory, computer-readable medium of claim 31, wherein the image data is received by an image analysis NN of the plurality of data-specific NNs, and the preselected encoding scheme used by the imagine analysis NN comprises a feature vector comprising a data shape of the image information at the intermediate layer, and wherein the data shape includes a number of set of molecular data points being analyzed, and a number of features contained in each feature vector for each specific molecular data point.

33. The non-transitory, computer-readable medium of claim 31, wherein the patient biopsy sample comprises a patient skin sample and the complete prognosis output comprises an indication of a risk level of metastasis of melanoma in the patient biopsy sample.

34. The non-transitory, computer-readable medium of claim 31, wherein the molecular output information comprises an indication of a likelihood of metastasis of melanoma in the patient biopsy sample, and
concatenation of the encoded molecular data to the image data comprises modifying, in accordance with the encoded molecular information, a feature vector of the image analysis NN at the intermediate layer.

35. The non-transitory, computer-readable medium of claim 31, wherein the molecular NN comprises a one-dimensional NN, and
the image analysis NN comprises a multi-dimensional convolutional NN (CNN).

36. The non-transitory, computer-readable medium of claim 31, wherein the one or more processors are further configured to:
receive patient data corresponding to the patient biopsy sample; apply the patient data to a patient information NN;
produce, based on the patient information and the patient information NN, patient output information;
generate encoded patient data by encoding the patient output information according to the preselected encoding scheme; and
concatenate the encoded patient data to the encoded molecular information and the image information at the intermediate layer of the image analysis NN.

37. The non-transitory, computer-readable medium of claim 36, wherein
the patient output information comprises an indication of a risk level of metastasis of melanoma in the patient biopsy sample, and
concatenation of the encoded patient data to the image data comprises modifying, in accordance with the encoded patient data, a feature vector of the image analysis NN at the intermediate layer.

38. The non-transitory, computer-readable medium of claim 31, wherein the one or more processors are further configured to:

receive clinical notes data corresponding to the patient biopsy sample; apply the clinical notes data to a clinical note NN;

produce, based on the clinical notes data and the clinical note NN, clinical note output information;

generate encoded clinical notes data by encoding the clinical note output information according to the pre-selected encoding scheme; and concatenate the encoded clinical notes data to the encoded molecular data and the image data at the intermediate layer of the image analysis NN.

39. The non-transitory, computer-readable medium of claim 38, wherein the clinical note output information comprises an indication of a risk level of metastasis of melanoma in the patient biopsy sample, and concatenation of the encoded notes data to the image data comprises modifying, in accordance with the encoded clinical note information, a feature vector of the image analysis NN at the intermediate layer.

* * * * *